United States Patent
Burn et al.

(10) Patent No.: US 7,083,862 B2
(45) Date of Patent: Aug. 1, 2006

(54) DENDRIMERS

(75) Inventors: Paul Leslie Burn, Oxford (GB); Ifor David William Samuel, Fife (GB); John Mark Lupton, Fife (GB); Richard Beavington, Kent (GB)

(73) Assignee: Isis Innovation Limited, Oxford (GB)

(*) Notice: Subject to any disclaimer, the term of this patent is extended or adjusted under 35 U.S.C. 154(b) by 72 days.

(21) Appl. No.: 10/203,448

(22) PCT Filed: Feb. 9, 2001

(86) PCT No.: PCT/GB01/00522

§ 371 (c)(1),
(2), (4) Date: Nov. 13, 2002

(87) PCT Pub. No.: WO01/59030

PCT Pub. Date: Aug. 16, 2001

(65) Prior Publication Data

US 2003/0134147 A1 Jul. 17, 2003

(30) Foreign Application Priority Data

Feb. 9, 2000 (GB) .................................. 0002936.3

(51) Int. Cl.
*H01L 51/50* (2006.01)
*C09K 11/06* (2006.01)
*H05B 33/14* (2006.01)
*C07C 211/55* (2006.01)
*C08G 83/00* (2006.01)

(52) U.S. Cl. ...................... 428/690; 428/917; 313/504; 313/506

(58) Field of Classification Search ................ 428/690, 428/917; 313/504, 506
See application file for complete search history.

(56) References Cited

U.S. PATENT DOCUMENTS 4,769,302 A 9/1988 Ueda

FOREIGN PATENT DOCUMENTS

| DE | 19541113 A1 | 4/1997 |
|---|---|---|
| EP | 0 517 542 A1 * | 6/1992 |
| EP | 506493 A2 | 9/1992 |
| EP | 996177 A2 | 4/2000 |
| JP | 11-74079 * | 3/1999 |
| WO | WO 99/21935 A1 | 5/1999 |

OTHER PUBLICATIONS

JP 11-074079 (published Mar. 1999) abstract and Japanese Patent Office machine translation.*

(Continued)

*Primary Examiner*—Dawn Garrett
(74) *Attorney, Agent, or Firm*—Quarles & Brady LLP

(57) ABSTRACT

A compound of formula (I), where x is 3, 2 or 1, y is 0 or 1, $n^1$ and $n^2$, which may be the same or different, are 0 or 1 to 3, X represents a divalent mono- or poly-aromatic and/or heteroaromatic moiety, the or each Y, which may be the same or different if x is 1, represents hydrogen or an optionally substituted hydrocarbon group, Z represents an aromatic group, or an inherently at least partly conjugated dendritic molecular structure comprising one or more aromatic and/or heteroaromatic groups and, optionally, alkenylene groups, connected to each other either directly or via a carbon atom of an alkenylene group, if present, to a ring carbon atom of an (hetero) aromatic group to which more than one at least partly conjugated dendritic chain is attached, said molecular structure being connected to the remainder of the molecule via a ring carbon atom, one or more of the (hetero) aromatic rings of the dendrimers optionally being substituted, Z and/or the remainder of the molecule, excluding any groups Y, being luminescent, with the proviso that when Z represents an aromatic group y must be 1.

20 Claims, 22 Drawing Sheets

OTHER PUBLICATIONS

Miller et al., "Electrically Conducting Dendrimers", J. Am. Chem. Soc. 1997, 119, p. 1005-1010, (no month).

Shirota et al., "Multilayered organic electroluminescent device using a novel starburst molecule, as a hole transport material", Appl. Phys. Lett. 65 (7) Aug. 1994, p. 807-809.

Wang et al., "Electroluminescent Diodes from a Single-Component Emitting Layer of Dendritic Macromolecules", Advanced Materials, 1996, 8, No. 3, p. 237-241, (no month).

Pillow et al., "A Facile Iterative Procedure for the Preparation of Dendrimers Containing Luminescent Cores and Stilbene Dendrons", Macromolecules, Sep. 1999, p. 5985-5993.

Halim et al., "Conjugated Dendrimers for Light-Emitting Diodes: Effect of Generation", Advanced Materials, 1999, p. 371-374, (no month).

Burn et al., "Effect of generation on the electronic properties of light-emitting dendrimers", SPIE, Jul. 1999, p. 66-74.

Sander, et al., "Synthesis, Properties, and Guest-Host Systems of Triphenylamine—based Oligo(arylenevinylene)s", Macromolecules, 1996, 29, pp. 7705-7708.

English Language Abstract for JP 11 074079.

English Language Abstract for JP 01 106070.

English Language Abstract for JP 01 105955.

English Language Abstract for JP 01 013553.

Jiang et al., "Organic light-emitting diodes made with poly(N-vinylcarbazole) (PVK) and 8-hydroxyquinoline aluminum (Alq3)", Synthetic Metals 87 (1997) 175-178.

English Language Abstract for DE 19541113.

* cited by examiner-

Synthesis of the zeroeth generation dendrimer

Triarylamine core + [phosphonate reagent] $\xrightarrow[\text{THF, r.t., 15.5 h.}]{\text{KO}^t\text{Bu}}$ 86%

(i) Excess potassium-*t*-butoxide, tetrahydrofuran, $2_R$, 21.5 h

DENDRIMERS

This invention relates to improved dendrimers which are light-emitting, to a novel process for making dendrimers and to devices using them.

Organic and polymer light emitting diodes (LEDs) have been the focus of intensive research for the past decade. Whereas small organic molecules are processed by thermal evaporation under high vacuum, polymers may be deposited directly from solution. Both classes of materials have their merits, with small organic molecules allowing greater chemical and colour purity and polymers greatly simplifying the manufacturing process which has led, for example, to displays produced by inkjet printing. An alternative approach is conjugated dendrimers which have been used successfully both as charge transporting and light-emitting materials. This class of materials combines a well defined chromophore and molecular mass with advantageous solution processing properties. With dendrimers it is possible to tune the emission colour independently of the processing properties.

The role of the degree of intermolecular interactions in conjugated polymers and their effect on optical and transport properties has been a topic of intense debate over the past few years. In the context of organic LEDs it is particularly important to understand the relationship between good transport properties and efficient luminescence. It is known that intermolecular interactions can quench the luminescence, but would increase wave function overlap of the π-electrons and so be beneficial to charge transport. The present invention relates to a class of dendrimers which allows a direct control of the microscopic packing through chemical modification and this provides a unique correlation between chemical structure of the molecules and macroscopic device properties. The degree of interaction between

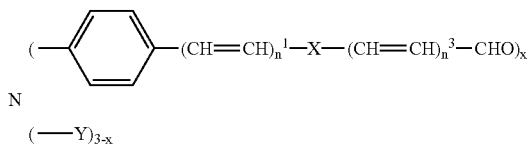

molecules as well as the film morphology and microscopic packing can be controlled by the dendrimer generation. Electrochemical studies on conjugated dendrimers have shown that charge injection takes place into the core and not into dendrons which have a wider energy gap. The dendrons act as spatial separators and insulate the cores. We have found that the electronic properties, such as barrier to charge injection in dendrimer-based LEDs, can remain unaffected by generation but that the change in chromophore separation directly affects the charge transport properties.

According to the present invention there is provided a compound of the formula:

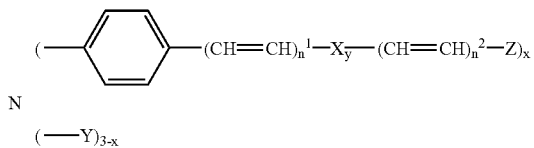

where x is 3, 2 or 1, y is 0 or 1, $n^1$ and $n^2$, which may be the same or different, are 0 or 1 to 3, X represents a divalent mono- or poly-(i.e. 2 or more) aromatic and/or heteroaromatic moiety, the or each Y, which may be the same or different if x is 1, represents hydrogen or an optionally substituted hydrocarbon group, Z represents an aromatic group, or an inherently at least partly conjugated dendritic molecular structure comprising one or more aromatic and/or heteroaromatic groups and, optionally, alkenylene groups, connected to each other either directly or via a carbon atom of an alkenylene group, if present, to a ring carbon atom of an (hetero) aromatic group to which more than one at least partly conjugated dendritic chain is attached, said molecular structure being connected to the remainder of the molecule via a ring carbon atom, one or more of the (hetero) aromatic rings of the dendrimers optionally being substituted, Z and/or the remainder of the molecule, excluding any groups Y, being luminescent with the proviso that when Z represents an aromatic group y must be 1.

It will be appreciated that the compounds of the present invention contain 1 to 3 dendritic molecular structures attached to the central nitrogen atom via the

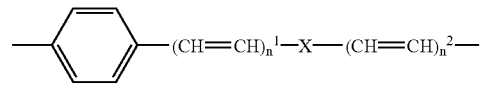

grouping. It is preferred that x is 3 in which case Y is absent.

Figure 1:
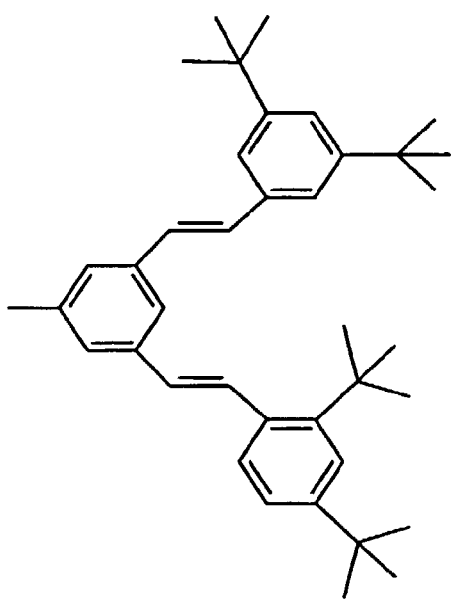
FIG. 1 shows a preferred group Z for compounds used in the invention.

As indicated, Y can represent hydrogen or an optionally substituted hydrocarbon group. The nature of the hydrocarbon group is not particularly critical although, typically, it is an alkyl or aryl group such as an alkyl group of 1 to 6 carbon atoms, for example methyl or a phenyl group, an alkylaryl or arylalkyl group, or an arylvinylaryl group such as a stilbene group. When x is 1, each Y can be the same or different.

It will be noted that the dendritic structures Z are connected, directly or indirectly, to the central nitrogen atom via a benzene ring. The nature of X can be broad and can represent a mono or poly-aromatic and/or hetero aromatic moiety such as a moiety of pyridine (as in divinyl pyridine), pyrimidine, triazine, thiophene, (as in divinylthiophene), oxadiazole and coronene as well as benzene (as in divinylbenzene and distyrylethylene) and anthracene or can represent linked phenylene units. It can also represent a polyaromatic moiety wherein the aromatic rings are connected by a conjugated grouping such as a vinyl grouping. A typical example is

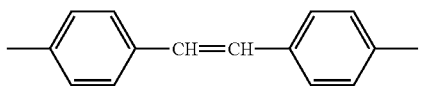

Preferably X represents a moiety of benzene. The group X is preferably linked to the vinyl groups in the para position although it can also be linked in the ortho or meta position. For anthracene the links are preferably para in the central ring.

$n^1$ and $n^2$ independently represent 0, 1, 2 or 3. Thus, the length of the conjugated structure can vary although it is preferred that $n^1$ and $n^2$ are both equal to 1. Thus the preferred unit incorporating the vinyl groups is distyryl benzene. A preferred grouping with $n^1=n^2=1$ is trans, trans-distyryl benzene.

The various aromatic and heteroaromatic rings present in the compound may be substituted, for example by $C_1$ to $C_{15}$ alkyl or alkoxy groups, preferably alkyl or alkoxy of 1 to 8, for example 1 to 6, carbon atoms such as t-butyl or 2-ethyl hexyl. It will be appreciated, in this connection, that the benzene ring which is adjacent to the nitrogen atom can likewise be substituted.

In Z, the aromatic groups are preferably benzene rings, preferably substituted at 3 and 5 positions, pyridine or triazine rings or linked phenylene units. These rings may optionally be substituted in the same manner as the other rings present in the molecule. Z incorporates conjugated units which are preferably based on arylenes and heteroarylenes optionally linked by alkenyl (preferably vinyl) groups. The conjugation of the core may be varied both in length, with the aim to have the HOMO-LUMO energy gap lower than that of the branches as aforesaid, and in substituent pattern. This allows control of the colour of emission, from blue to red. Electron affinity can be controlled by the choice of core.

When Z is an aromatic group by itself, this group is typically a benzene group other than unsubstituted benzene and preferably 3,5-disubstituted benzene, or a heteroaromatic group such as pyridine or triazine, or linked phenylene units. These rings may be substituted in the same manner as the other rings.

The compounds typically have one or more end or surface groups which will be attached to the terminal ring or rings of Z. With higher-generation dendrimers (see hereinafter), the surface groups may tend to assume a majority or substantially all fo the molecular contact with the surrounding environment. Therefore, the outer surface controls the solubility and processability of the molecule in common solvents and thus changes to the internal electronic structure of the chromophore(s) can be possible without unacceptably affecting the processing properties and vice versa. If the need arises for multilayer LEDs to be prepared, then the surface groups may be selected to allow crosslinking or appropriate solubility.

The dendrimers of this invention provide an opportunity of optimising the electronic and processing properties independently which should give improved manufacturability of electronically optimised materials. Some examples of the surface groups which would be suitable to incorporate onto the dendrimers include branched and unbranched alkyl, especially t-butyl, branched and unbranched alkoxy, for example 2-ethyl-n-hexyloxy, hydroxy, alkylsilane, carboxy, carbalkoxy, and vinyl. A more comprehensive list include a further-reactable alkene, (meth)acrylate, sulphur-containing or silicon-containing group; sulphonyl group; polyether group; $C_1$-to $C_{15}$ alkyl or alkoxy (preferably t-butyl) group; amine group; mono-, di- or tri $C_1$-to $C_{15}$ alkylamine group; —COOR group wherein R is hydrogen or $C_1$-to $C_{15}$ alkyl or alkenyl; —O$_2$SR group wherein R is $C_1$-to-$C_{15}$ alkyl or alkenyl; —SR group wherein R is aryl, or $C_1$-to-$C_{15}$ alkyl or alkenyl; —SiR$_3$ groups wherein the R groups are the same or different and are hydrogen $C_1$-to-$C_{15}$ alkyl or alkenyl, or —SR' group (R' is aryl or $C_1$-to-$C_{15}$ alkyl or alkenyl), aryl or heteroaryl.

The most preferred surface group is t-butyl. Thus particularly preferred groups Z have the formulae shown in FIGS. 1 to 4 and 24 of the accompanying drawings.

Z can also represent an aromatic group, preferably a phenyl group which can also be substituted with one or more surface groups as discussed above, Preferably, therefore, in this embodiment Z represents a 3,5-di(t-butyl) phenyl group. When Z represents an aromatic group in this way, the dendrimer will be the 0-generation dendrimer while when Z represents the value shown in FIG. 1 this corresponds to generation 1 of the dendrimer.

Figure 2:
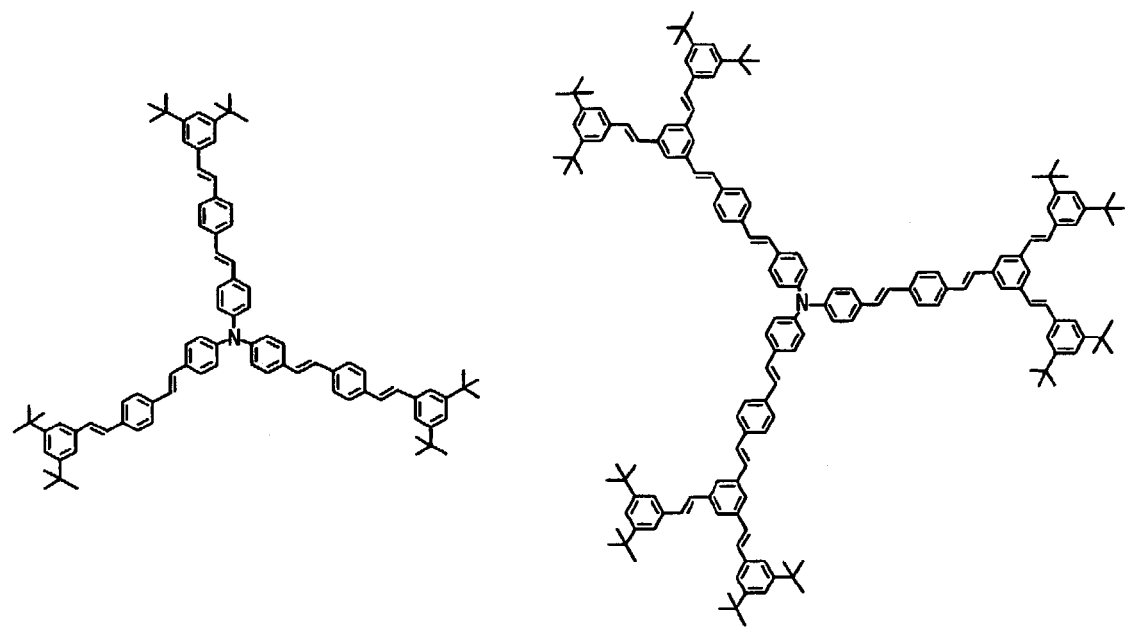
FIGS. 2 to 4 show preferred compounds used in the invention.
Figure 3:
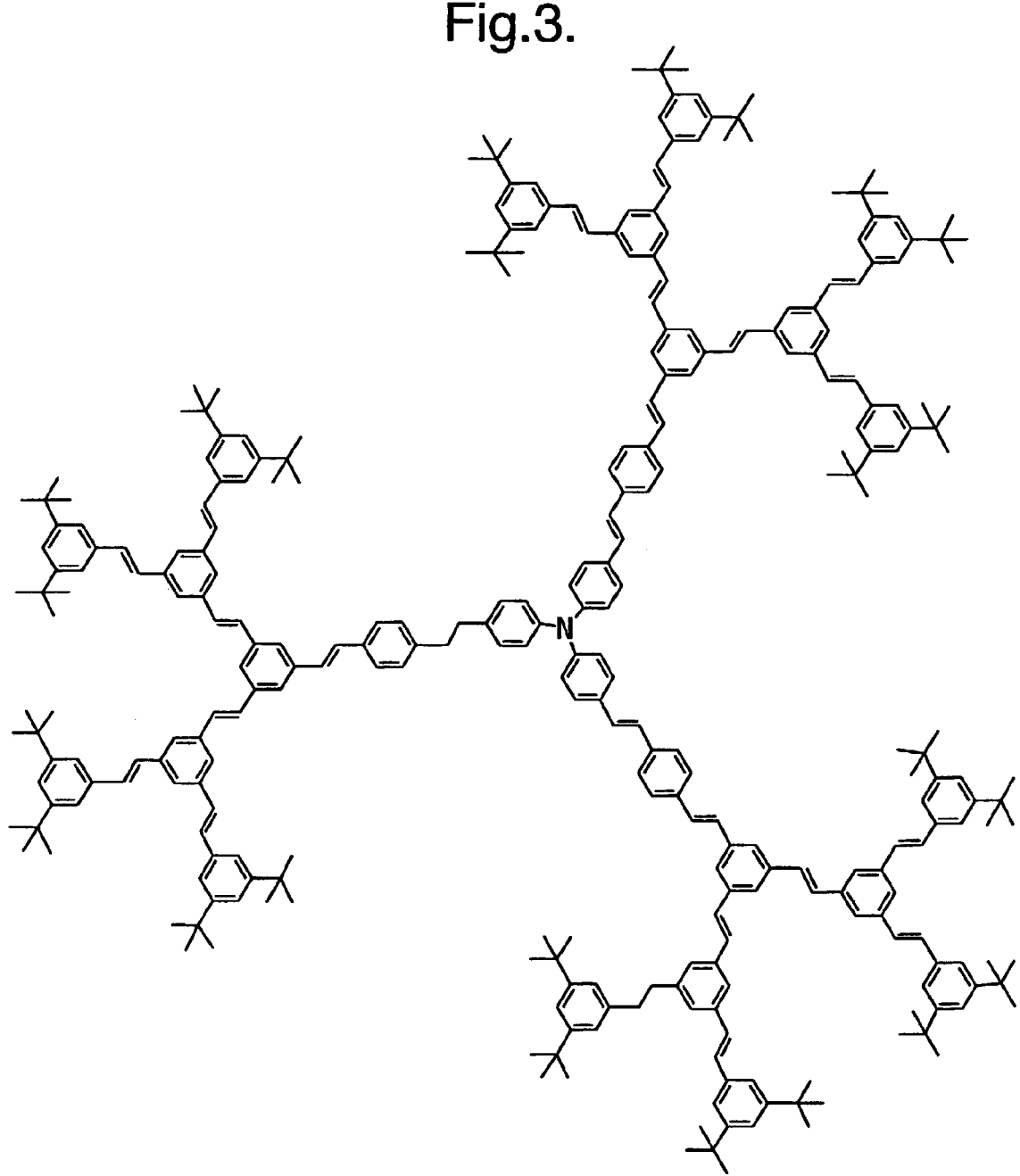
Figure 4:
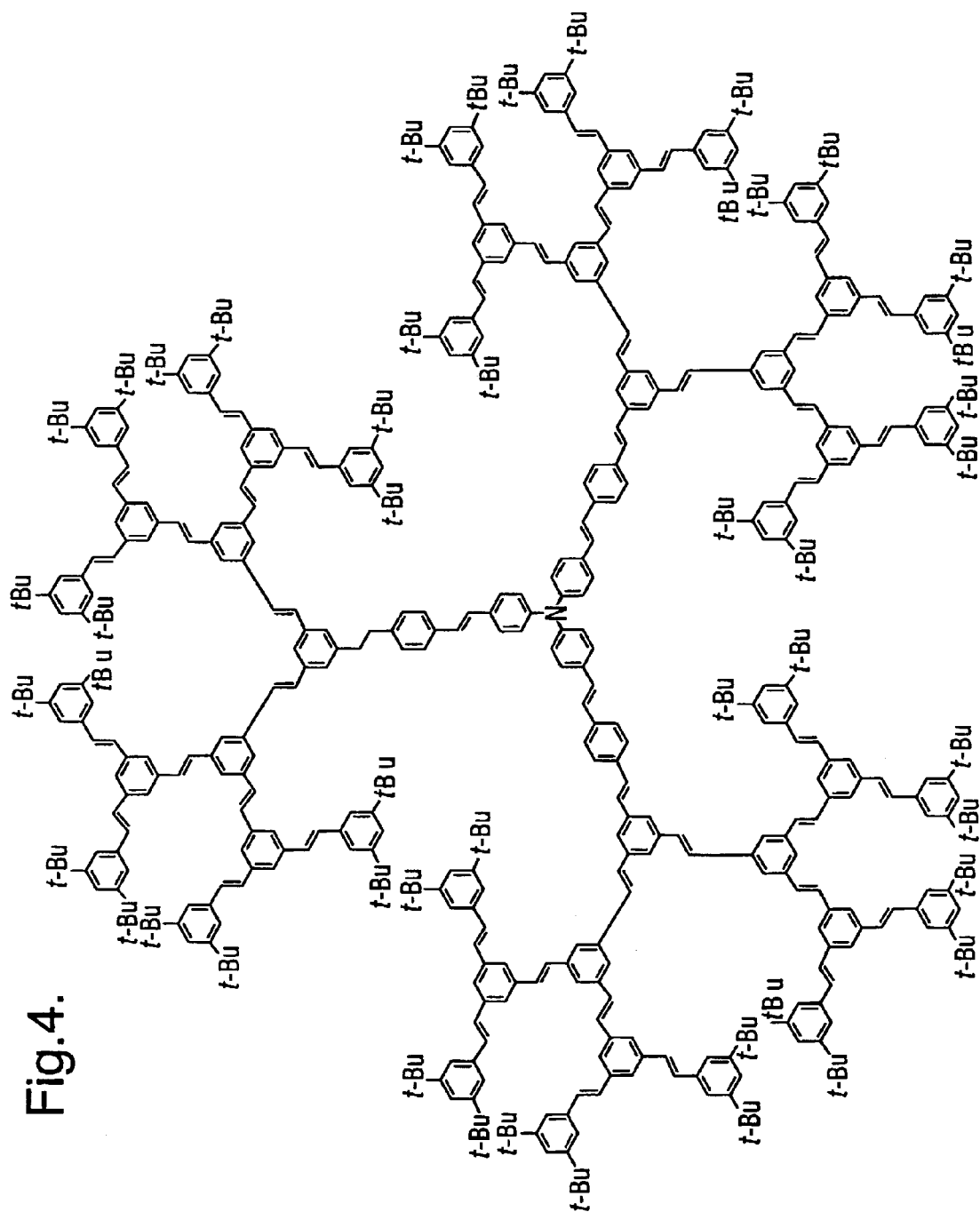

Preferred compounds of the present invention include those shown in FIGS. 2, 3 and 4, these being the 0- and 1-generation, 2-generation and 3-generation, respectively. The radii of these molecules are 10.3 Å, 14.6 Å, 19.4 Å and 24.0 Å, respectively, as estimated from gel permeation chromatography.

The compound may have more than one luminescent moiety and the energy resulting from electrical or optical excitation is transferred to one of them for light emission. In a preferred embodiment the dendrimer incorporates at least one inherently at-least-partly-conjugated luminescent moieties which moieties may or may not be conjugated with each other, wherein the or each said dendritic structure(s) include(s) at least one of the said luminescent moieties, the luminescent moiety or moieties further from the core of the dendrimer being of larger HOMO-LUMO energy gap than the luminescent moiety or moieties closer to or partly or wholly within the core of the dendrimer. In another embodiment the HOMO-LUMO energy gap is the same.

The relative HOMO-LUMO energy gaps of the moieties can be measured by methods known per se using a UV-visible spectrophotometer. One of the luminescent moieties may be, or (partly or wholly) within, the core itself i.e. the part of the molecule excluding Z, which will thus preferably have a smaller inherent HOMO-LUMO gap energy than the other luminescent moiety or moieties in the dendritic structures. Alternatively, or in addition, the dendritic structures themselves may each contain more than one luminescent moiety, in which case those further from the core will again preferably have larger inherent HOMO-LUMO gap energies than those closer to the core. In this case, the core itself need not be luminescent, although luminescent cores are generally preferred. Again any groups Y can also be luminescent.

It is furthermore possible to control the electron affinity of the dendrimers by the addition to the chromophores of electron-withdrawing groups, for example cyano and sulfone which are strongly electron-withdrawing and optically transparent in the spectral region we are interested in. Alternatively the branches and/or core may contain heteroaromatic units such as pyridine, pyrimidine, thiazole, triazine or fluorinated aryl or heteroaryl units to increase the electron affinity of the dendrimer.

Intermolecular interactions have a strong effect on the photophysics of conjugated molecules, and the flexibility of synthesis (generation number, surface groups, linkers, etc.) will allow them to be controlled. This is believed to be a particular advantage for the efficiency of blue emission, because it will tend to prevent the blue luminescence from being quenched by excimer formation, which may render the emission yellow instead. In addition, luminescence in dyes and the like is often quenched at high concentrations, as encountered in the film. By incorporating these molecules into a dendrimer we can avoid this, for example, by avoiding processes such as pi-stacking.

With dendrimers exciton migration to quenching sites can be inhibited, optimised chromophores can be used, and intermolecular interactions controlled to avoid undesirable processes such as excimer formation. In linear conjugated polymers the exciton migrates through the sample to regions of low HOMO-LUMO gap energy and can often encounter defects which quench the luminescence. Dendrimers can be designed according to the present invention so that the innermost or central chromophore has a lower HOMO-LUMO energy gap than chromophores closer to the surface. The excitations are localised on the core and migration to quenching sites is impeded. In addition, this process will tend to give rise to a space charge build-up similar to that obtained in organic light emitting devices incorporating a hole-blocking electron transporting layer. Dendrimers with electron-withdrawing groups attached to the chromophores and/or high electron affinity chromophores will be easier to prepare as the routes involve "small molecule" reactions, which do not have the same stringent requirements, for example, yield, of those for forming high polymers.

The compounds of the present invention possess particular advantages over other dendrimers. In particular, they possess enhanced stability which results in devices using them to have an increased life.

The compounds of the present invention can be processed in solution i.e. a solution of the compound can be applied as a layer of a display device and then the solvent evaporated. This is a much simpler procedure than vacuum deposition which is currently generally needed because individual molecular chromophores such as those included within dendrimers are not often solution processable.

It has also been found that the compounds of the present invention can act both as a hole transport layer and/or as a light emitting layer, with appropriate other layers, in a display device. This naturally gives rise to increased versatility of the compounds.

It has surprisingly been found that charge mobility can be controlled by altering the generation of the dendrimer. In other words by measuring the mobility of successive generations it can be readily established what generation is needed to give the desired degree of mobility. This provides a way of controlling the operating bias and current of an organic LED. The low charge mobility of some of the compounds of the present invention gives rise to increased efficiency.

The dendrimers of this invention may appear fully conjugated. However, as the branch linkages are typically all meta in arrangement, the pi-electron system is not fully delocalised over the whole molecule (R. S. Kang et al, *J. Chem. Soc., Chem. Comm.* 1996, 1167). This means that in a simple analysis the central core can be considered independently from the branches when determining the required colour of light emission and the relative energy gaps or conjugation lengths.

The present invention also provides a process for preparing the compounds of the present invention which comprises reacting an aldehyde of the formula:

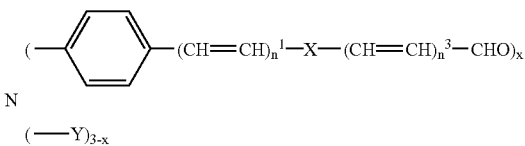

with a Z-containing compound of the formula:

TCH$_2$Z wherein Y, n$^1$, X, x and Z are as defined above, n$^3$ is 0, 1 or 2, and T represents a functional group which allows the adjacent methylene group to react with an aldehyde group to form an alkene.

One of skill in the art will be well aware of the functional groups which will cause the adjacent methylene group to react with the aldehyde group to form an alkene. Examples include phosphonium and phosphonate which is preferred i.e. the compound is (RO)$_2$P(O)CH$_2$Z where each R, which may be the same or different, represents an alkyl or aryl group.

The precise nature of the groups R is relatively unimportant although economic considerations will affect the choice. Typically R represents an alkyl group of 1 to 6 carbon atoms such as methyl.

The aldehyde starting material is typically obtained by reacting a bromide of the formula:

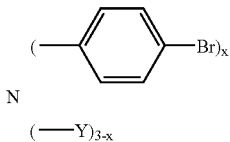

with a vinyl compound of the formula:

(CH$_2$=CH)$_n$$^3$—X—CHO

In order to obtain the phosphonate it is possible to react the corresponding aryl methyl bromide with the corresponding phosphate. The aryl methyl bromide itself can conveniently be obtained by reducing an aldehyde of formula OCH—Z, for example with a borohydride and then brominating the corresponding alcohol.

It will be appreciated that in order to obtain the 0 generation compound Z will represent an aromatic group; to obtain a generation 1 and successive generations Z represents the dendritic molecular structure. This is generally obtainable from the corresponding aldehyde. Successive generations can therefore readily be obtained.

It will be appreciated that this process differs from the process disclosed in our earlier W099/21935 where the aldehyde of the dendron moiety is reacted with a functional group. In contrast, in the process of the present invention a functional group of the dendron moiety is reacted with an aldehyde moiety containing the central nitrogen atom. A particular advantage of this procedure is that, as will be appreciated, it is difficult to form the core material with, say, three phosphonate groups, let alone purify it. This applies equally to the preparation of other dendrimers which require more than 2 phosphonate groups to form a core of the type disclosed in our earlier W099/21935 i.e. it is generally much easier to prepare an aldehyde of the core moiety, especially where more than 2 dendritic structures are to be attached to it. Accordingly, the present invention also provides a process for preparing a compound of the formula:

CORE-[DENDRITE]$_n$

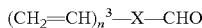

in which CORE represents an atom or group, n represents an integer of at least 1 and DENDRITE, which may be the same or different if n is greater than 1, represents an inherently at least partly conjugated dendritic molecular structure comprising aryl and/or heteroaryl groups and alkenyl groups connected to each other via a carbon atom of an alkenyl group to a ring carbon atom of an aryl or heteroaryl group, CORE terminating in the first single bond which is connected to a ring carbon atom of an (hetero) aryl group to which more than one at least partly conjugated dendritic chain is attached, said ring carbon atom forming part of DENDRITE, the CORE and/or DENDRITE being luminescent, which comprises reacting an aldehyde of the central atom or group with an aryl or heteroaryl compound bearing a functional group which allows the adjacent methylene group to react with an aldehyde to form an alkene thus resulting in the formation of CORE-DENDRITE.

CORE-DENDRITE can have any of the values disclosed in W099/21935, to which reference should be made for further details. It is particularly useful where the CORE is centered on a 1,3,5-substituted benzene ring.

The dendrimers of the present invention find utility in light emitting devices (LED). Accordingly, the present invention also provides a light emitting device comprising at least one compound of the present invention. Typically the LED comprises two electrodes with 1 or more layers therebetween, at least one of said layers is, or contains, a compound of the present invention. As indicated above, a particular feature of the compounds of the present invention is that they can act both as light emitters and/or charge transporting layers, depending on the other materials present. Thus in a "single layer" device the compound acts as a light emitter. On the other hand, in a "bi-layer device" the compound can form a hole transporting layer together with a light emitter such as an aluminium quinolinate. Alternatively, bi-layers formed with an electron transport layer such as PBD (2-phenyl-5-biphenyl-1,3,4-oxadiazole) which has a wide gap cause the dendrimer to act as a light emitter. On the other hand, with an organolanthanide layer emission can come from the organolanthanide and/or from the dendrimer.

The general construction of the light emitting devices can be conventional although it is a particular feature of the present invention that the compounds of the present invention are solution processable such that they can be applied to the device in the form of a solution in a common solvent such as tetrahydrofuran, for example by spin coating, and then the solvent evaporated. In general the dendrimer layer will be adjacent to one electrode, typically an indium tin oxide layer, with the extra layer over it before the cathode, typically of aluminium or MgAl, layer. If desired a buffer layer, for example of poly(3,4-ethylenedioxythiophene) and polystyrene sulphonate, can be placed between the dendrimer layer and the indium tin oxide layer.

The light emitting devices of the present invention can form part of a colour display device including pixels. Indeed the compounds can be used in any semi-conductor device, for example a photodiode, solar cell, FET or solid state triode.

The following Examples further illustrate the present invention. In these Examples G-O, G-1 etc, indicates zero generation, 1$^{st}$ generation etc. while the compounds prepared are as shown in FIGS. 2 to 4.

EXAMPLE 1—[G-0]$_3$N

Figure 18:
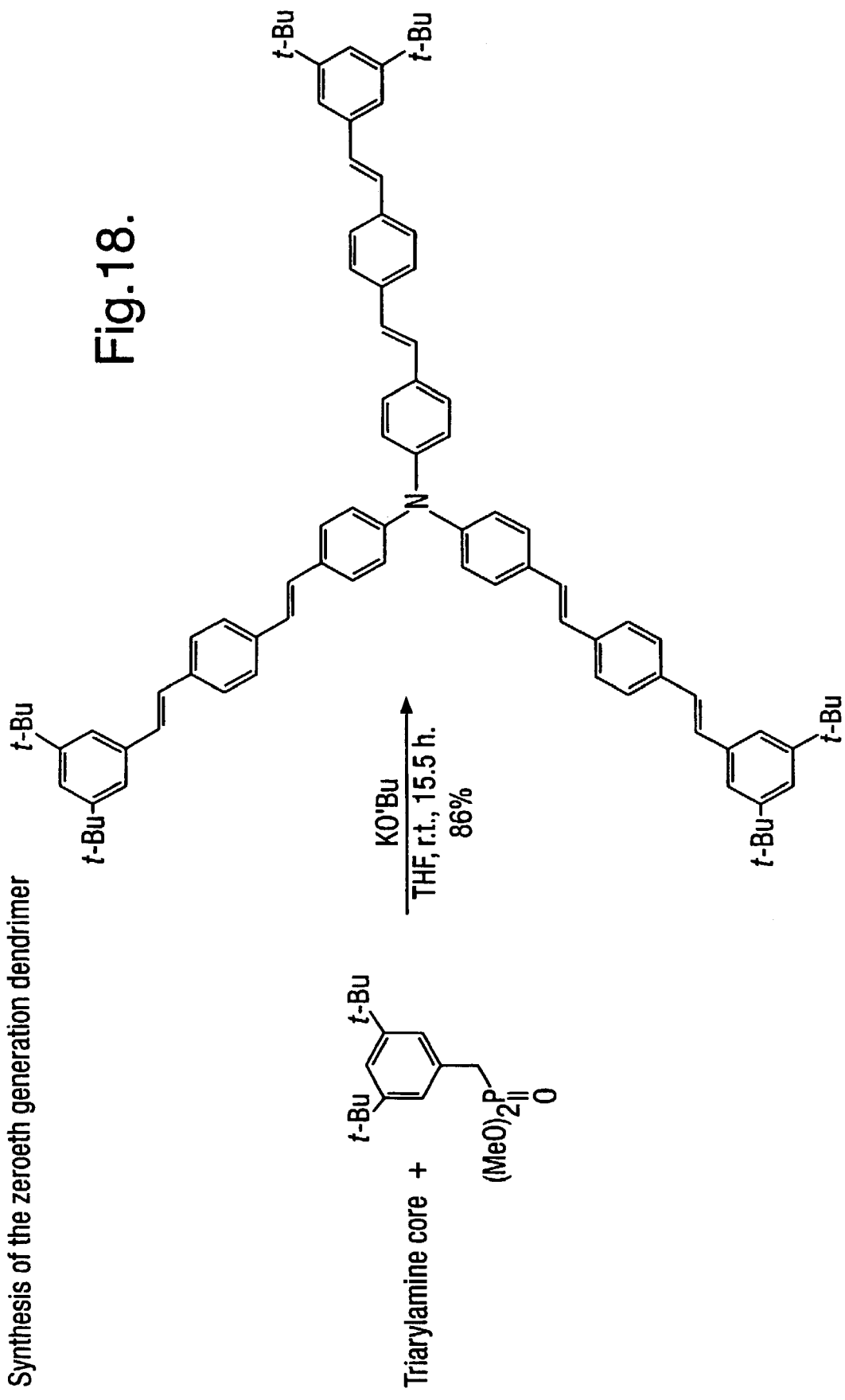
FIG. 18 shows the reaction scheme for preparing a zero-generation compound for use in the invention.

A mixture of 1-(methylenedimethylphosphonate)-3,5-di-tert-butylbenzene (986 mg, 3.16 mmol), tris[4-(4'-formylstyryl)phenyl]amine (498 mg, 0.78 mmol) and potassium tert-butoxide (353 mg, 3.15 mmol) in tetrahydrofuran (80 cm$^3$) was stirred at room temperature under argon for approximately 16 h, giving a fluorescent yellow solution. FIG. 18 shows the reaction scheme. Water (25 cm$^3$) and dichloromethane (175 cm$^3$) were added, the organic layer separated, dried over sodium sulphate, filtered, and the solvent removed to give a yellow solid residue. Purification by column chromatography, gradient eluting from dichloromethane-light petroleum (1:4) to dichloromethane, gave [G-0]$_3$N (804 mg, 86%) as a bright yellow solid, mp 182° C. (Found: C, 90.15; H, 8.17; N, 1.20. C$_{90}$H$_{99}$N requires C, 90.48; H, 8.35; N, 1.17%); $\lambda_{max}$(CH$_2$Cl$_2$)/nm (log $\epsilon$) 241 (4.72), 341 (4.91) and 421 (5.13); $\lambda_H$(400 MHz, CDCl$_3$) 1.38 (54H, s, t-Bu), 7.05 and 7.19 (6H, ABq, J 16.5, 7', 8'-H), 7.09 and 7.14 (6H, ABq, J 6, 7", 8"-H), 7.14 and 7.45 (12H, AA'BB', 2, 3, 5, 6-H), 7.37 (3H, dd, J 1.5, 4''-H), 7.39 (6H, d, J 1.5, 2'', 6''-H), 7.53 (12H, AA'BB', 2'3'5'6'-H); m/z (FAB) 1194.8 (M$^+$, 100%).

EXAMPLE 2—[G-1]$_3$N

A mixture of 1-(methylenedimethylphosphonate)-3,5-bis (3',5'-di-tert-butylstyryl)benzene (1.19 g, 1.89 mmol), tris [4-(4'-formyl)styrylphenyl]amine (302 mg, 0.475 mmol) and potassium tert-butoxide (212 mg, 1.89 mmol) in tetrahydrofuran (60 cm$^3$) was stirred at room temperature under argon for 14 h. The solvent was removed. Water (25 cm$^3$) and dichloromethane (50 cm$^3$) were added. The organic layer was separated, washed with brine (100 cm$^3$), dried over sodium sulphate, filtered and the solvent removed to give a yellow solid residue. Purification by column chromatography over silica, gradient eluting from dichloromethane-light petroleum (1:4) to dichloromethane—light petroleum (1:2) gave [G-1]$_3$N (817 mg, 81%) as a bright yellow solid, mp 238–239° C. (Found: C, 90.54; H, 8.80; N, 0.63. C$_{162}$H$_{183}$N requires C, 90.74; H, 8.60; N, 0.65%); $\lambda_{max}$(CH$_2$Cl$_2$)/nm (log $\epsilon$) 239 (4.99), 323 (5.31), 334sh (5.29) and 4.23 (5.17); $\delta_H$(400 MHz, CDCl$_3$) 1.40 (108H, s, t-Bu), 7.05–7.31 (30H, m, vinylic-H and 2, 6-H), 7.40 (6H, dd, J 1.5, 4'''-H), 7.44 (12H, d, J 1.5, 2''', 6'''-H), 7.47 (6H, ½AA'BB', 3, 5-H), 7.56 (12H, AA'BB', 2', 3', 5', 6'-H), 7.61 (6H, br s, 2'', 6''-H) and 7.64 (3H, br s, 4''-H); m/z (MALDI) 2143.5 (M$^+$, 100%.

EXAMPLE 3—[G-2]$_3$N

A mixture of 1-(methylenedimethylphosphonate)-3,5-bis [3',5'-bis(3'',5''-di-tert-butylstyryl)styryl]benzene (1.01 g, 0.80 mmol), tris[4-(4'-formyl)styrylphenyl]amine (129 mg, 0.203 mmol) and potassium tert-butoxide (93 mg, 0.829 mmol) in tetrahydrofuran (40 cm$^3$) was stirred at room temperature under argon for approximately 14 h. The solvent was removed by rotary evaporation. Water (25 cm$^3$) and dichloromethane (50 cm$^3$) were added. The organic layer was separated, washed with brine (100 cm$^3$), dried over sodium sulphate, filtered and the solvent removed to give a yellow solid residue. Purification by column chromatography over silica, gradient eluting from dichloromethane—light petroleum (1:4) to dichloromethane—light petroleum (1:2) gave [G-2]$_3$N (611 mg, 76%) as a bright yellow solid, mp 268° C. (Found: C, 90.58; H, 9.18; N, 0.35. C$_{306}$H$_{351}$N requires C, 90.90; H, 8.75; N, 0.35 %); $\lambda_{max}$(CH$_2$Cl$_2$)/nm (log $\epsilon$) 239 (5.25), 323 (5.73), 334sh (5.70) and 423 (5.18); $\delta_H$(400 MHz, CDCl$_3$) 1.41 (216H, s, t-Bu), 7.06–7.34 (54H, m, vinylic-H and 2, 6-H), 7.41 (12H, dd, J 1.5, 4''''-H), 7.45 (24H, d, J 1.5, 2'''', 6''''-H), 7.48 (6H, ½AA'BB', 3, 5-H), 7.58 (12H, AA'BB', 2'3'5'6'-H), 7.67 (24H, m, 2'', 6'', 2''', 4''', 6'''-H) and 7.71 (3H, br s, 4''); m/z (MALDI) 4042.8 (M$^+$, 100%).

EXAMPLE 4—[G-3]$_3$N

Figure 19:
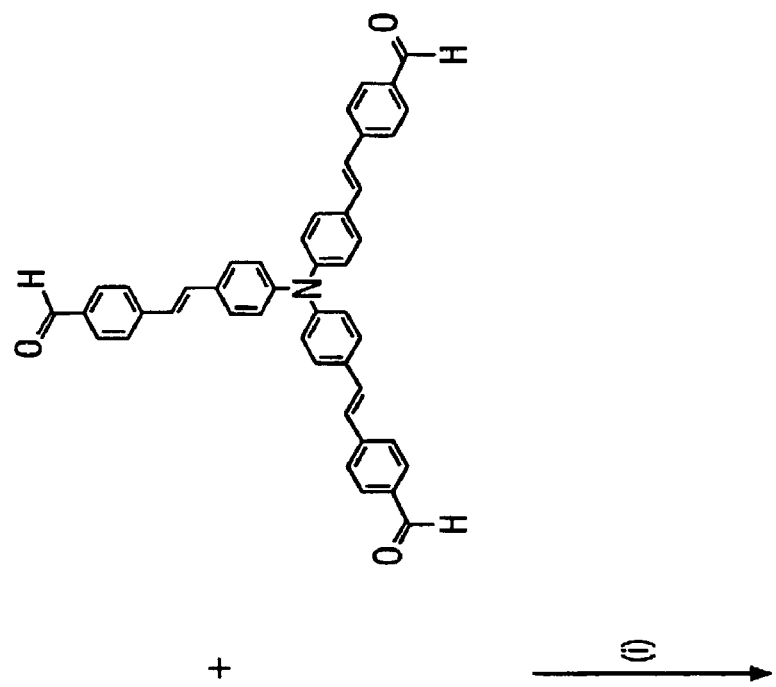
FIG. 19 shows the reaction scheme for preparing a third-generation compound for use in the invention.
Figure 19:
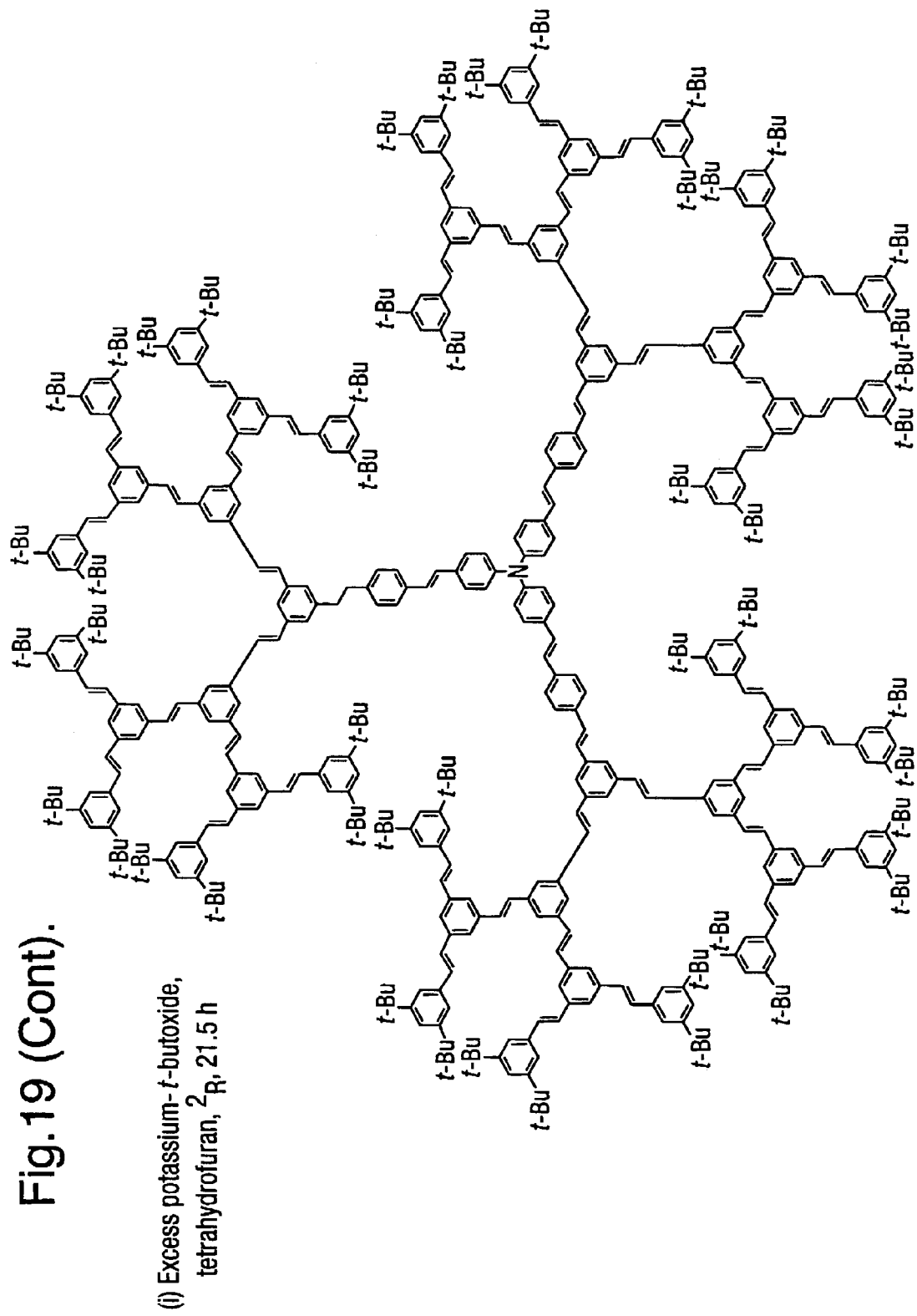

Potassium tert-butoxide (171 mg, 1.52 mmol) was added to a solution of tris[4-(4'-formyl)styrylphenyl]amine (51.5 mg, 0.074 mmol) and 1-(methylenedimethylphosphonate)-3,5-bis{3',5'-bis[3'',5''-bis(3''',5'''-di-tert-butylstyryl)styryl] styryl}benzene (759 mg, 0.30 mmol) heated at reflux. FIG. 19 shows the reaction scheme. The solution immediately turned a dark red-brown colour. The mixture was heated at reflex for approximately 18 h and allowed to cool. Water (50 cm$^3$) and dichloromethane (50 cm$^3$) were added. The aqueous layer was separated and extracted with dichloromethane (2×50 cm$^3$). The combined organic layers were washed with brine (50 cm$^3$), dried over sodium sulphate, filtered, and the solvent removed to leave a yellow solid. Purification by column chromatography using dichloromethane—light petroleum (2:3) as eluent, then recrystallisation from a dichloromethane-methanol mixture gave [G-3]$_3$N (349 mg, 60%) as a yellow powder, mp 266–267° C. (Found: C, 90.56; H, 9.29; N, 0.0. C$_{594}$H$_{687}$N requires C, 90.99, H, 8.83; N, 0.18%); $\lambda_{max}$(CH$_2$Cl$_2$)/nm (log$\epsilon$) 239 (5.52), 323 (6.08), 334sh (6.04) and 423.69 (5.16); $\delta_H$(400 MHz, CDCl$_3$) 1.40 (432H, s, t-Bu), 7.08–7.36 (102 H, m, vinylic-H and 2, 6-H), 7.39 (24H, dd, J 1.5, 4'''''-H), 7.45 (48H, d, J 1.5, 2''''', 6'''''-H), 7.50 (6H, ½AA'BB', 3, 5-H), 7.61 (12H, AA'BB', 2', 3', 5', 6'-H), 7.68–7.76 (63H, m, 2'', 6'', 4''', 2''', 4'''', 6'''', 2''''', 4''''', 6'''''-H); m/z (MALDI) 7839.1 (M$^+$, 100%).

EXAMPLE 1A

[G-0]Phosphonate 1-(methylenedimethylphosphonate)-3,5-di-tert-butylbenzene

Figure 20:
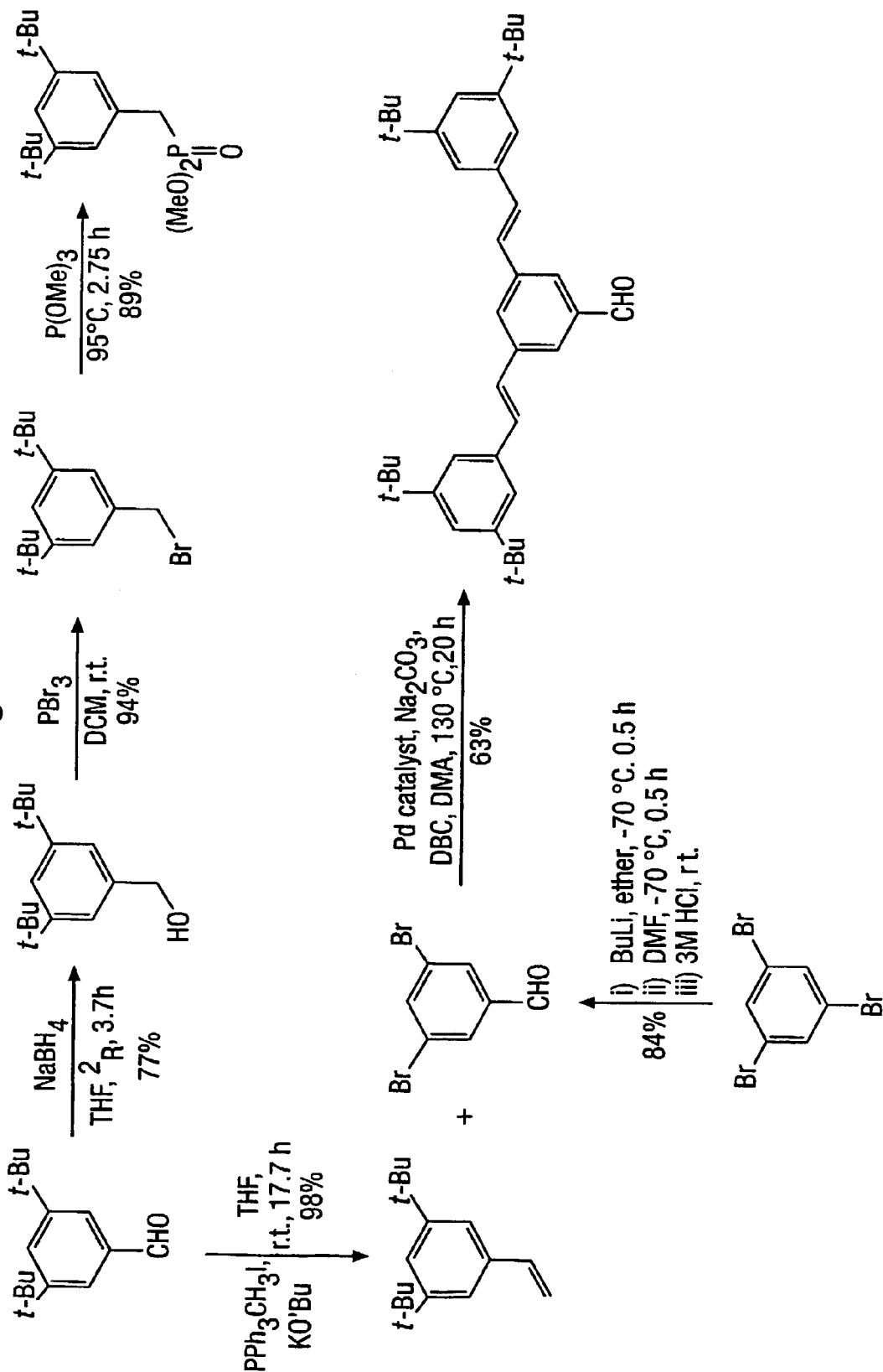
FIG. 20 shows the reaction scheme for preparing an intermediate compound for use in the invention.

A mixture of 3,5-di-tert-butylbenzyl bromide (1.86 g, 6.57mol) and trimethylphosphite (7.6 cm$^3$, 64 mmol) were stirred at 95° C. for approximately 3 h, then allowed to cool. FIG. 20 gives the reaction scheme and the route to the starting material for Example 2C. The solution was diluted with ether (25 cm$^3$) and washed with water (6×25 cm$^3$), dried over sodium sulphate, filtered and the solvent removed to give a colourless oil which was dried under vacuum giving 1-(methylenedimethylphosphonate)-3,5-di-tert-butylbenzene (1.82 g, 89%) as a white crystalline solid, mp 56° C.; $\delta_H$(200 MHz, CDCl$_3$) 1.33 (18H, s, t-Bu), 3.18 (2H, d, J 21.5, 7-H), 3.66 (6H, d, J 11, OCH$_3$), 7.15 (2H, br s, 2, 6-H) and 7.32 (1H, br s, 4-H); m/z (APCI+) 313.2 (MH$^+$, 100%) and 335.2 (MNa$^+$, 15%).

EXAMPLE 2A

[G-1]Phosphonate 1-(methylenedimethylphosphonate)-3,5-bis(3',5'-di-tert-butylstyryl)benzene A mixture of 3,5-bis(3',5'-di-tert-butylstyryl)styryl]benzyl bromide (500 mg, 0.52 mmol) and trimethylphosphite (5.0 cm$^3$, 38 mmol) was heated at 110° C. for 3 h. Methanol (100 cm$^3$) was added and water was added slowly until a precipitate was formed. The precipitate was filtered and dried under vacuum to give 1-(methylenedimethylphosphonate)-3,5-bis(3',5'-di-tert-butylstyryl)benzene (477 mg, 91%). A sample for analysis was recrystallised from a dichloromethane-methanol-water mixture, mp 207–208° C. (Found: C, 78.24; H, 9.44. C$_{41}$H$_{57}$O$_3$P requires C, 78.31; H, 9.14%); $v_{max}$(CHCl$_3$)/cm$^{-1}$ 1596s (C=C), 1062 (P—O—C), 1038s (P—O—C) and 964s (C=C—H trans); $\lambda_{max}$ (CHCl$_3$)/nm (log $\epsilon$) 308 (4.75), 3.16 (4.75) and 331sh (4.60); $\delta_H$(500 MHz, CDCl$_3$); 1.38 (36H, s, t-Bu), 1.23 (2H, d, J 22, CH$_2$), 3.72 (6H, d, J 11, OCH$_3$), 7.12 and 7.23 (4H, d, J 16, 7', 8'-H), 7.38 (4H, m, 2, 6, 4'-H), 7.40 (4H, d, J 1.5, 2', 6'-H), 7.62 (1H, m, 4-H); m/z (APCI+) 630 (MH$^+$, 100%).

EXAMPLE 3A

[G-2]Phosphonate 1-(methylenedimethylphosphonate)-3,5-bis [3',5'-bis(3'',5''-di-tert-butylstyryl) styryl]benzene A mixture of 3,5-bis([3',5''-bis(3'',5''-di-tert-butylstyryl) styryl]styryl benzyl bromide (1.24 g, 1.00 mmol) and trimethylphosphite (10 cm$^3$) was heated at 100° C. under argon for 18 h. Excess trimethylphosphite was removed by distillation under reduced pressure and the white solid residue was recrystallised from a dichloromethane-methanol mixture. Column chromatography, eluting with dichloromethane, gave 1-(methylenedimethylphosphonate)-3,5-bis [3',5'-bis(3",5"-di-tert-butylstyryl)styryl] benzene (983 mg, 78%) as a white solid, mp>220° C. (decomp) (Found: C, 84.63; H, 9.03. $C_{89}H_{113}PO_3$ requires C, 84.72; H, 9.03%); $v_{max}$(KBr)/cm$^{-1}$ 1595 (C═C), 1056 and 1028 (P—O—C) and 958 (C═C—H trans); $\lambda_{max}$(CH$_2$Cl$_2$)/nm (log δ) 230 (4.69) and 321 (5.24); $\lambda_H$(400 MHz, CDCl$_3$) 1.40 (72H, s, t-Bu), 3.26 (2H, d, J 21.5, CH$_2$P), 3.76 (6H, d, J 11, OCH$_3$), 7.19 and 7.30 (8H, ABq, J 16, 7", 8"-H), 7.27 (4H, s, 7', 8'-H), 7.40 (4H, br s, 4"-H), 7.44 (10H, br s, 4', 2", 6"-H), 7.64 (6H, br s, 2, 6, 2', 6'-H) and 7.70 (1H, br s, 4-H); m/z (CI+) 1261.8 (MH$^+$, 100%).

EXAMPLE 4A

[G-3]Phosphonate 1-(methylenedimethylphosphonate)-3,5-bis{3',5'-bis[3",5"-bis(3'",5'"-di-tert-butylstyryl)styryl]styryl}benzene Trimethylphosphite (5.4 cm$^3$, 46 mmol) was added to 3,5-bis{3',5'-bis[3",5"-bis(3'",5'"-di-tert-butylstyryl)styryl]styryl}benzyl bromide (1.14 g, 0.455 mmol) and the suspension heated at 100° C. under argon for 2 h. Excess trimethylphosphite was removed by distillation under reduced pressure. The residue was recrystallised from a dichloromethane-methanol mixture, then further purified by column chromatography over silica using dichloromethane as eluent, giving 1-(methylenedimethylphosphonate)-3,5-bis{3',5'-bis[3",5"-bis(3'",5'"-di-tert-butylstyryl)styryl]styryl}benzene (853 mg, 74%) as a white solid, mp 232° C. (Found: C, 87.30; H, 9.18. $C_{185}H_{225}PO_3$ requires C, 87.90; H, 8.97); $v_{max}$(KBr)/cm$^{-1}$ 1594 (C═C), 1059 and 1033 (P—O—C) and 960 (C═C—H trans); $\lambda_{max}$(CH$_2$Cl$_2$)/nm (log ε) 322 (5.59) and 334sh (5.50); $\delta_H$(400 MHz, CDCl$_3$) 1.39 (144H, s, t-Bu), 3.38 (2H, d, J 21, CH$_2$P), 3.79 (6H, d, J 11, OCH$_3$), 7.19 and 7.32 (16H, ABq, J 16, 7'", 8'"-H), 7.30 (4H, s, 7', 8'-H), 7.33 (8H, s, 7", 8"-H), 7.38(8H, dd, J 1.5, 4'"-H), 7.44 (16H, d, J 1.5, 2'", 6'"-H), 7.48 (2H, br s, 4'-H), 7.66 (4H, s, 4"-H), 7.67 (8H, s, 2", 6"-H), 7.67 (5H, br s, 4, 2', 6'-H), 7.73 (2H, s, 2, 6-H); m/z (MALDI) 2527.8 (M$^+$, 100%) and 2590.7 (MCu$^+$, 97%).

EXAMPLE 2B

[G-1]CH$_2$Br 3,5-bis(3',5'-di-tert-butylstyryl)benzyl bromide

Phosphorus tribromide (2.8 cm$^3$, 30 mmol) was added to a solution of 3,5-bis(3',5'-di-tert-butylstyryl)benzyl alcohol (1.60 g, 3.0 mmol) in dichloromethane (50 cm$^3$) and the mixture stirred at room temperature for 3 h. Propan-2-ol (14 cm$^3$) was added slowly and the solvent was completely removed. The residue was purified by column chromatography over silica, eluting with dichloromethane-light petroleum (40–60) (1:9), giving 3,5-bis(3',5'-di-tert-butylstyryl) benzyl bromide (1.52 g, 85%). A sample for analysis was recrystallised from a dichloromethane-light petroleum (60–80) mixture, mp 222–223° C. (Found: C, 77.75; H, 8.72. $C_{39}H_{51}Br$ requires C, 78.11; H, 8.57%); $v_{max}$(CHCl$_3$)/cm$^{-1}$ 1596s (C═C) and 964s (C═C—H trans); $\lambda_{max}$(CHCl$_3$)/nm (log ε) 315 (4.82); $\delta_H$(400 MHz, CDCl$_3$) 1.38 (36H, s, t-Bu), 4.55 (2H, s, CH$_2$), 712 and 7.24 (4H, d, J 16, 7', 8'-H), 7.39 (2H, dd, J 1.5, 4'-H), 7.41 (4H, d, J 1.5, 2', 6'-H), 7.47 (2H, d, J 1, 2, 6-H) and 7.63 (1H, m, 4-H); m/z (APCI+) 521 ((M-Br)$^+$, 100%) and 599 (M$^+$, 40%).

EXAMPLE 3B

[G-2]CH$_2$Br 3,5-bis [3'5'-bis(3",5"-di-tert-butyl) styryl)styryl]benzyl bromide A solution of 3,5-bis[3'5'-bis(3",5"-di-tert-butylstyryl)styryl]benzyl alcohol (2.43 g, 2.08 mmol) and phosphorus tribromide (2.0 cm$^3$) in dichloromethane (50 cm$^3$) was stirred at room temperature under argon for 46 h. Water (100 cm$^3$) was added carefully and dichloromethane (150 cm$^3$) was added. The organic layer was separated and washed with aqueous sodium bicarbonate solution (5%, 100 cm$^3$), water (100 cm$^3$) and brine (2×100 cm$^3$), dried over sodium sulphate, filtered and the solvent removed. Purification by column chromatography over silica, eluting with dichloromethane, gave 3,5-bis[3'5'-bis(3",5"-di-tert-butyl)styryl) styryl]benzyl bromide (1.43 g, 56%) as a white solid, $\delta_H$(500 MHz, CDCl$_3$) 1.41 (72H, s, t-Bu), 4.60 (2H, s, CH$_2$Br), 7.19 and 7.30 (8H, ABq, J 16.5, 7", 8"-H), 7.28 (4H, s, 7', 8'-H), 7.40 (4H, dd, J 1.5, 4"-H), 7.44 (8H, d, J 1.5, 2", 6"-H), 7.52 (2H, d, J 1, 2, 6-H), 7.64 (4H, br s, 2', 6'-H) 7.65 (2H, br s, 4'-H) and 7.71 (1H, br s, 4-H); m/z (FAB) 1232.5 (M$^+$, 100%).

EXAMPLE 4B

[G-3]CH$_2$Br 5-bis{3',5'-bis[3",5"-bis(3'",5'"-di-tert-butylstyryl)styryl]styryl}benzyl bromide Phosphorus tribromide (1.2 cm$^3$, 12.4 mmol) was added to a solution of 3,5-bis{3',5'-bis[3",5"-bis(3'",5'"-di-tert-butylstyryl)styryl]styryl}benzyl alcohol (3.009 g, 1.235 mmol) in dichloromethane (120 cm$^3$) and the yellow mixture stirred in the dark under argon for approximately 6 days. Water (50 cm$^3$) was added carefully, then ether (300 cm$^3$). The organic layer was washed with water (100 cm$^3$) and brine (70 cm$^3$), dried over sodium sulphate, filtered and the solvent removed. The residue was passed through a plug of silica, eluting with dichloromethane-light petroleum (2:3), giving 5-bis{3',5'-bis[3",5"-bis(3'",5'"-di-tert-butylstyryl)styryl]styryl}benzyl bromide (1.45 g, 47%) as a white solid. A sample for analysis was recrystallised from a dichloromethane-methanol mixture, mp 256–258° C. (Found: C, 87.74; H 8.46, $C_{183}H_{219}Br$ requires C, 87.97; H, 8.83); $v_{max}$(KBr)/cm$^{-1}$ 1594 (C═C) and 960 (C═C—H trans); $\lambda_{max}$(CH$_2$Cl$_2$)/nm (log ε) 323 (5.54) and 334sh (5.46); $\delta_H$(400 MHz, CDCl$_3$) 1.39 (144H, s, t-Bu), 4.62 (2H, s, CH$_2$Br), 7.19 and 7.31 (16H, ABq, J 16, 7'", 8'"-H), 7.30 (4H, s, 7', 8'-H), 7.33 (8H, s, 7", 8"-H), 7.39 (8H, dd, J 1.5, 4'"-H), 7.44 (16 H, d, J 1.5, 2'", 6'"-H), 7.57 (2H, br s, 4'-H), 7.66 (12H, br s, 2", 4", 6"-H), 7.68 (4H, br s, 2', 6'-H), 7.70 (1H, br s, 4-H) and 7.74 (2H, br s, 2, 6-H); m/z (MALDI) 2498.74 (M$^+$, 100%).

EXAMPLE 2C

[G-1]CH$_2$OH 3,5-bis(3',5'-di-tert-butylstyryl)benzyl alcohol

A mixture of 3,5-bis(3',5'-di-tert-butylstyryl)benzaldehyde (3.00 g, 6.61 mmol) and sodium borohydride (840 mg, 22.2 mmol) in tetrahydrofuran (150 cm$^3$) was heated at reflux for 110 min. The solvent was then completely removed and light petroleum (30–40) and aqueous hydrochloric acid (3 M, 30 cm$^3$) were added and stirred until effervescence had ceased. The white precipitate was then filtered and dried under vacuum to give 3,5-bis(3',5'-di-tert-butylstyryl)benzyl alcohol (2.63 g, 87%). A sample for analysis was recrystallised from a dichloromethane-light petroleum (60–80) mixture, mp 226–228° C. (Found: C, 87.28; H, 9.47. C$_{39}$H$_{52}$O requires C, 87.26; H, 9.76%); $v_{max}$(CHCl$_3$)/cm$^{-1}$ 3608w (OH), 1596 (C=C) and 964 (C=C—H trans); $\lambda_{max}$(CH$_2$Cl$_2$)/nm (log $\epsilon$) 230 (4.42), 307 (4.80), 312 (4.80), 315 (4.80) and 330sh (4.66); $\delta_H$(500 MHz, CDCl$_3$) 1.41 (36H, s, t-Bu), 1.81 (1H, t, J 6, OH), 4.79 (2H, d, J 6, CH$_2$), 7.16 and 7.27 (4H, d, J 16, 7', 8'-H), 7.40 (2H, dd, J 1.5, 4'-H), 7.43 (4H, d, J 1.5, 2', 6'-H), 7.49 (2H, s, 2, 6-H) and 7.66 (1H, s, 4-H); m/z (APCI+) 519 ((M—OH)$^+$, 100%).

Figure 21:
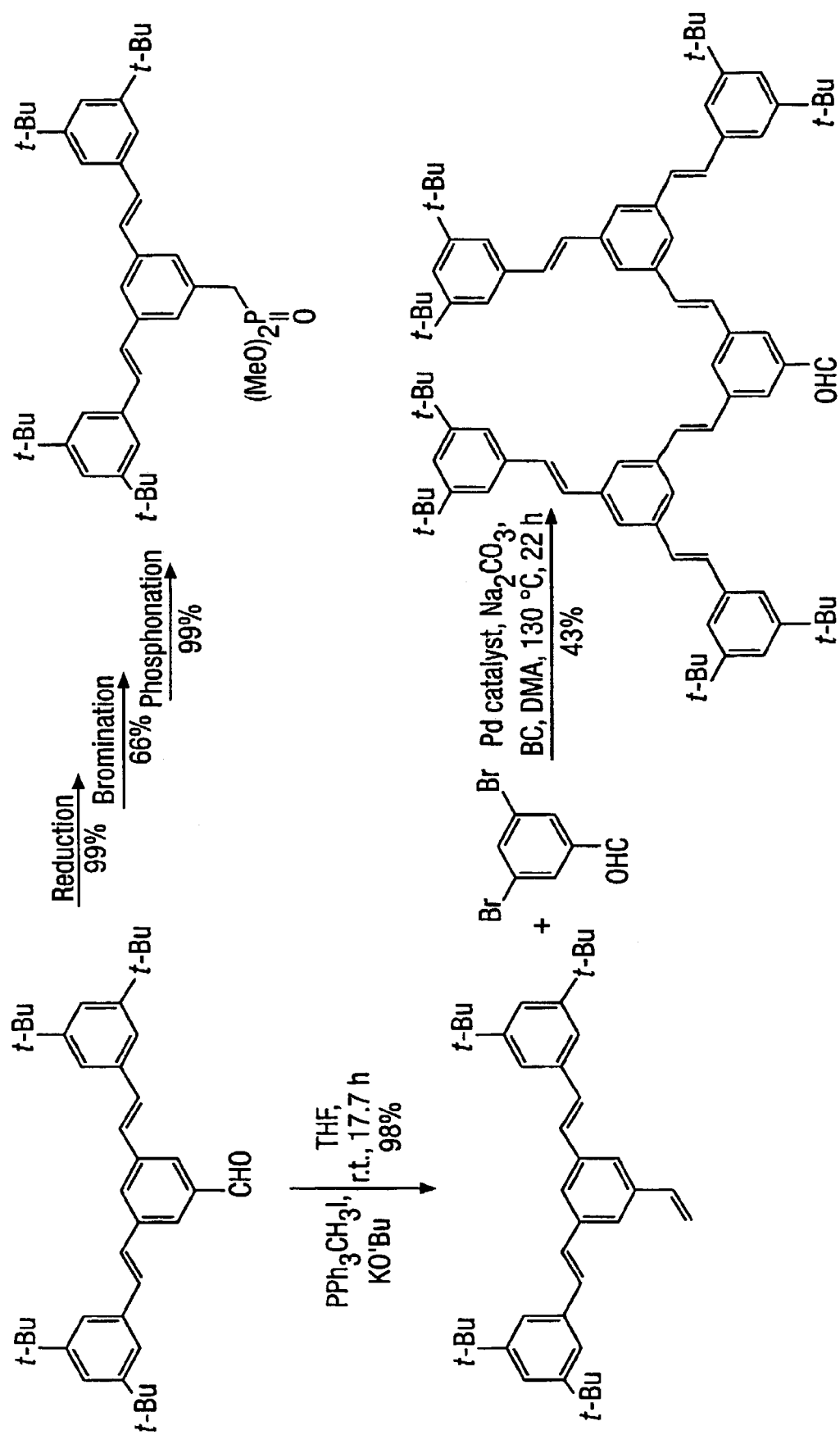
FIG. 21 shows the reaction scheme for preparing phosphonate and aldehyde intermediates for use in the invention.
Figure 21:
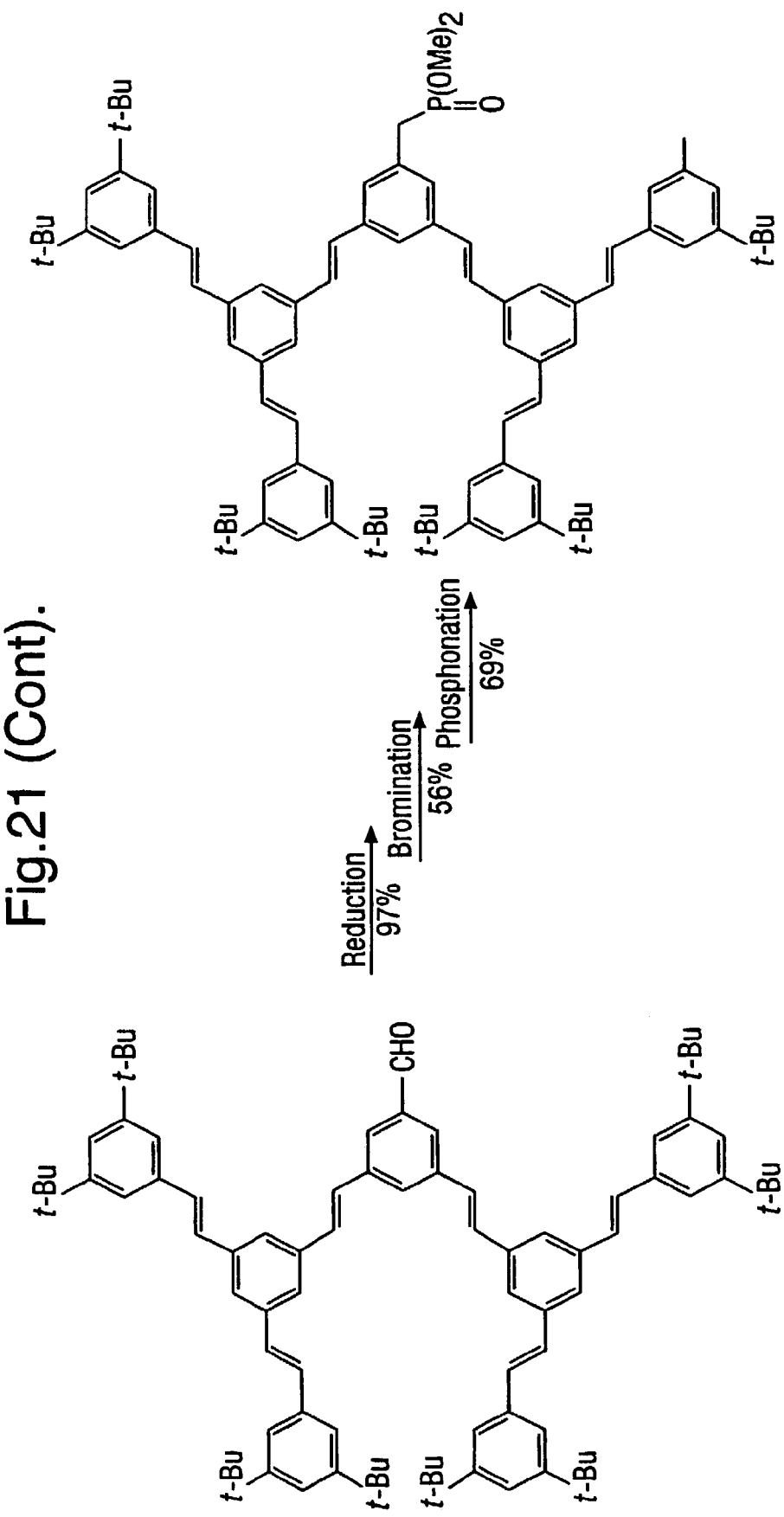

FIG. 21 gives the reaction scheme to produce the [G-1] phosphonate and also to the aldehyde starting material for Example 3C leading to the [G-2] phosphonate.

EXAMPLE 3C

[G-2]CH$_2$OH 3,5-bis[3'5'-bis(3'',5''-di-tert-butyl)styryl)styryl]benzyl alcohol A mixture of 3,5-bis[3'5'-bis(3'',5''-di-tert-butyl)styryl)styryl]benzaldehyde (2.52 g, 2.16 mmol) and sodium borohydride (164 mg, 4.34 mmol) in tetrahydrofuran (75 cm$^3$) was heated at reflux for 40 min. Water (50 cm$^3$) and dichloromethane (100 cm$^3$) were added. The aqueous layer was separated and extracted with dichloromethane (2×30 cm$^3$). The combined organic layers were washed with water (100 cm$^3$) and brine (100 cm$^3$), dried over sodium sulphate, filtered and the solvent removed to leave a white solid. The residue was purified by column chromatography over silica eluting with dichloromethane, giving 3,5-bis[3',5'-bis(3'',5''-di-tert-butyl)styryl)styryl]benzyl alcohol (2.43 g, 97%) as a white solid, mp 310° C. (Found: C, 89.38; H, 9.29. C$_{87}$H$_{108}$O requires C, 89.33; H, 9.31); $v_{max}$(KBr)/cm$^{-1}$ 3567 (OH), 1595 (C=C) and 961 (C=C—H trans); $\lambda_{max}$ (CH$_2$Cl$_2$)/nm (log $\epsilon$) 230 (4.86), 322 (5.43) and 330sh (5.34); $\delta_H$(400 MHz, CDCl$_3$) 1.41 (72H, s, t-Bu), 1.78 (1H, t, J 6, OH), 4.82 (2H, d, J 6, 7-H), 7.19 and 7.30 (8H, ABq, J 16.5, 7'', 8''-H), 7.30 (4H, s, 7', 8'-H), 7.40 (4H, dd, J 1.5, 4''-H), 7.45 (8H, d, J 1.5, 2'', 6''-H), 7.53 (2H, br s, 4'-H), 7.65 (6H, br s, 2, 6, 2', 6'-H) and 7.71 (1H, br s, 4-H); m/z (FAB) 1169.6 (M$^+$, 100%).

EXAMPLE 4C

[G-3]CH$_2$OH 3,5-bis{3',5'-bis[3'',5''-bis(3''',5'''-di-tert-butylstyryl)styryl]styryl}benzyl alcohol A solution of 3,5-bis{3',5'-bis[3'',5''-bis(3''',5'''-di-tert-butylstyryl)styryl]styryl}benzaldehyde (3.853 g, 1.585 mmol) in tetrahydrofuran (50 cm$^3$) was treated with sodium borohydride (121 mg, 3.20 mmol) and heated at reflux for 135 min. The solvent was removed. Dichloromethane (50 cm$^3$) was added and the solution washed with water (50 cm$^3$) and brine (50 cm$^3$), dried over sodium sulphate, filtered and the solvent removed to leave a yellow foam. The product was purified by column chromatography over silica, eluting with dichloromethane-light petroleum (2:3). Recrystallisation from a dichloromethane-methanol mixture gave 3,5-bis{3',5'-bis[3'',5''-bis(3''',5'''-di-tert-butylstyryl)styryl]styryl}benzyl alcohol (3.07 g, 80%) as a yellow powder, mp 248° C. (Found: C, 89.89; H, 8.89. C$_{183}$H$_{220}$O requires C, 90.24; H, 9.10%); $v_{max}$(KBr)/cm$^{-1}$ 3568 (OH), 1594 (C=C) and 959 (C=C—H trans); $\lambda_{max}$(CH$_2$Cl$_2$)/nm (log $\epsilon$) 323 (5.59) and 334sh (5.52); $\delta_H$(400 MHz, CDCl$_3$) 1.39 (144H, s, t-Bu), 1.80 (1H, t, OH), 4.85 (2H, d, CH$_2$OH), 7.19 and 7.31 (16H, ABq, J 16, 7''', 8'''-H), 7.32(4H, s, 7', 8'-H), 7.34(8H, s, 7'', 8''-H), 7.38 (8H, dd, J 1.5, 4'''-H), 7.44 (16H, d, J 1.5, 2''', 6'''-H), 7.57(2H, br s, 4'-H), 7.67 (12H, br s, 2'', 4'', 6''-H), 7.67 (4H, br s, 2', 6'-H), 7.70 (1H, br s, 4-H) and 7.74 (2H, br s, 2, 6-H); m/z (MALDI) 2434.94 (M$^+$, 100%).

EXAMPLE 1D

Amine trialdehyde core
tris[4-(4'-formylstyryl)phenyl]amine

Figure 22:
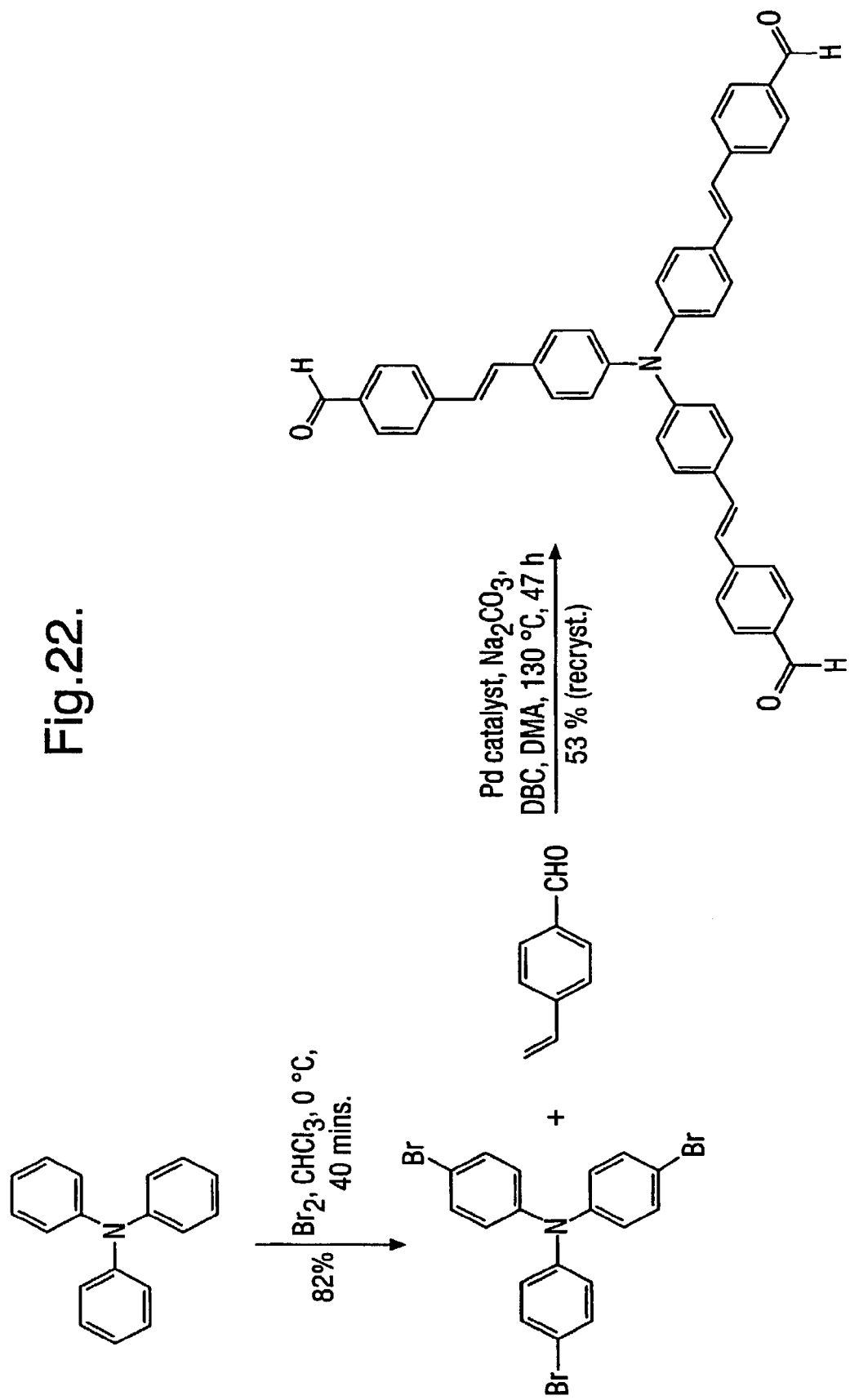
FIG. 22 shows the reaction scheme for preparing the core of a compound for use in the invention.

A mixture of tris(4-bromophenyl)amine (6.34 g, 13.1 mmol), 4-vinylbenzaldehyde (6.95 g, 53 mmol), 2,6-di-tert-butyl-p-cresol (11.57 g, 0.053 mmol), sodium carbonate (5.57 g, 53 mmol), trans-di($\mu$-aceto)-bis[o-(di-o-tolylphosphino)benzyl]dipalladium (II) (37 mg, 39 $\mu$mol) and N,N-dimethylacetamide (70 cm$^3$) was degassed by alternate exposure to high vacuum and purging with argon over 30 min. The mixture was heated at 130° C. under argon for 47 h, then allowed to cool. Aqueous hydrochloric acid (3 M, 10 cm$^3$) and chloroform (150 cm$^3$) were added. The organic layer was separated and washed with water (2×100 cm$^3$) and brine (100 cm$^3$), dried over sodium sulphate, filtered and the solvent removed to leave an orange residue which crystallised overnight with refrigeration. The residue was recrystallised from a dichloromethane-light petroleum mixture, leaving an impure orange solid. Purification by column chromatography, eluting with dichloromethane-ethyl acetate (19:1) gave tris[4-(4'-formylstyryl)phenyl]amine (4.47 g, 53%), mp 256–258° C. (Found: C, 84.81; H, 5.24; N, 2.21. C$_{45}$H$_{33}$NO$_3$ requires C, 85.02; H, 5.23; N, 2.20%); $v^{max}$(KBr)/cm$^{-1}$ 1691 (C=O); $\lambda_{max}$(CH$_2$Cl$_2$)/nm (log $\epsilon$) 432 (4.99) and 316 (4.76); $\delta_H$(500 MHz, CDCl$_3$) 7.07 and 7.24 (6H, ABq, J 16.5, vinylic-H), 7.15 and 7.48 (12H, AA'BB', 2, 3, 5, 6-H), 7.64 and 7.87 (12H, AA'BB', 2', 3', 5', 6'-H) and 9.99 3H, s, CHO); m/z (FAB) 635.2 (M$^+$, 100%). The reaction scheme is shown in FIG. 22.

EXAMPLE 5

Device Fabrication

Light emitting diodes (LEDs) were fabricated on indium tin oxide (ITO) substrates, which had previously been cleaned chemically (either ultrasonication in acetone and isopropanol (set A) or ultrasonication in ammonia and peroxide, subsequent baking (set B)). In all cases the dendrimers were spin-coated from tetrahydrofuran solutions of concentration 10 mg/ml. For set A a PEDOT (poly(3,4-ethylenedioxythiophene))/PSS (polystyrene sulphonate) layer was deposited onto the ITO; the dendrimer was subsequently spin coated on top of the PEDOT/PSS layer. Metal electrodes were subsequently thermally evaporated on top of the dendrimer layer. For set B the dendrimer was spin-coated onto the ITO and, if appropriate, the molecular materials were subsequently evaporated onto the dendrimer layer. For both sets, in the final step patterned metal electrodes (Al or MgAl) were evaporated onto the topmost layer. Measurements were performed in vacuum for set A and in air for set B.

Single Layer Devices

Aluminium Contacts (set A)

Figure 5:
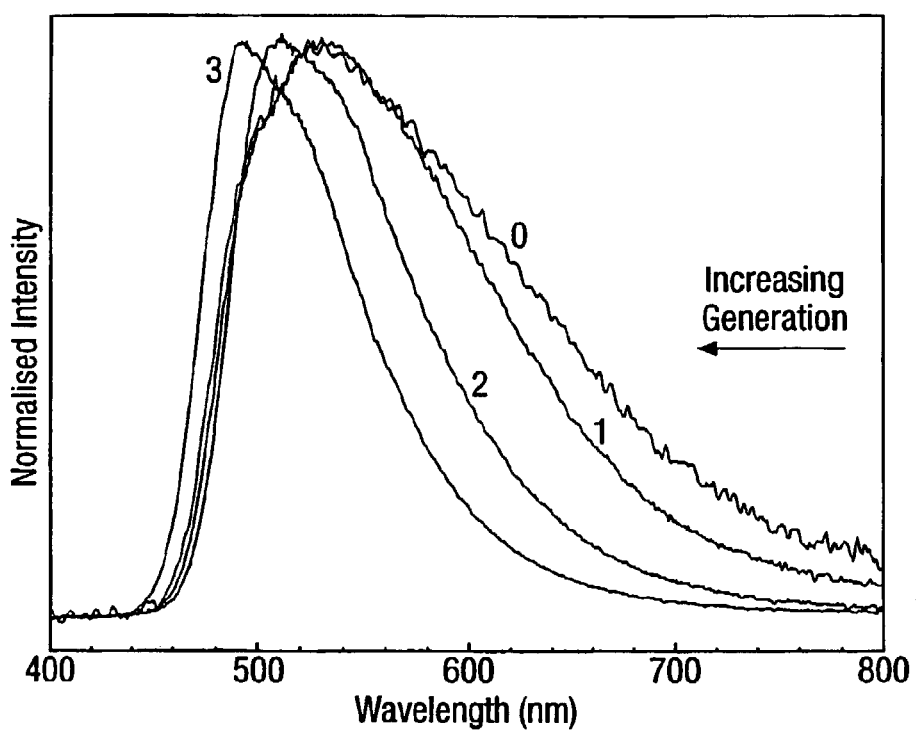
FIG. 5 shows the electroluminescence (EL) spectra of compounds used in the invention.

Single layer diodes were fabricated from the compounds of Examples 1 to 4 (referred to as 0 to 3 (corresponding to [G-0] to [G-3] respectively). The electroluminescence (EL) spectra are shown in FIG. 5, which show that the core of the material is a green emitter. The red tail is reduced as the generation increases. This may be due to a decrease in excimer formation or aggregation as the intermolecular interactions between chromophores are reduced with increasing generation.

Figure 6:
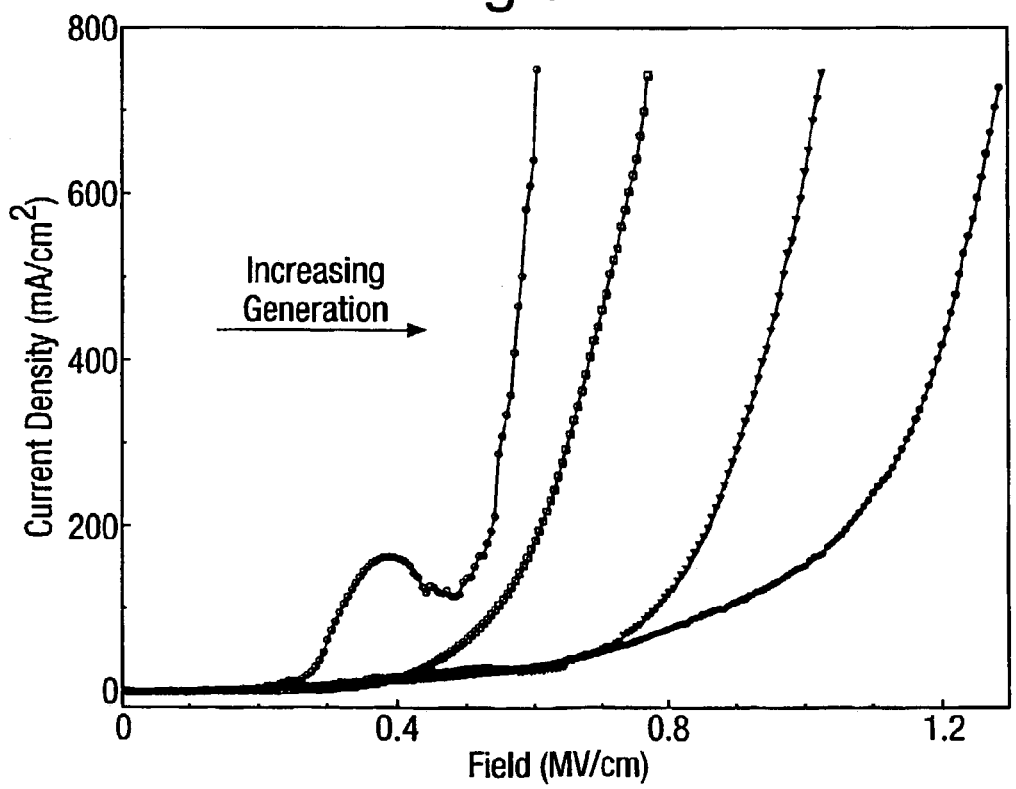
FIG. 6 shows the current-field characteristics of compounds used in the invention.

The current-field characteristics of the family of dendrimers are shown in FIG. 6. It is seen that the operating field increases with increasing generation and increasing chromophore spacing. This suggests that the transport capabilities of the material are reduced with increasing generation, which is a useful tool for tuning mobilities and can be exploited for balancing electron and hole currents in bilayer devices.

Figure 7:
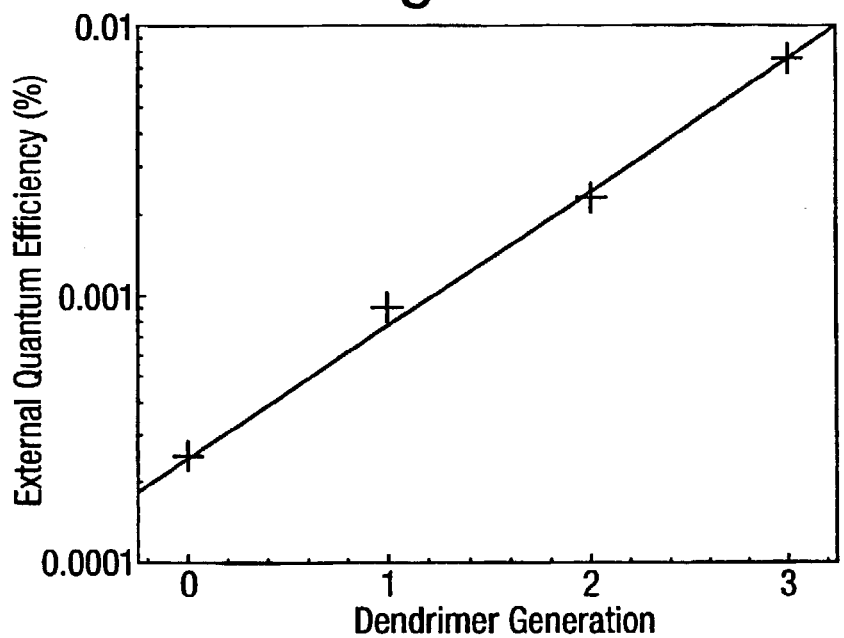
FIG. 7 shows the increase in quantum efficiency with increasing generation.

In single layer configuration, the change in device characteristics, which reflects the majority carrier properties (i.e. the hole transport properties), gives rise to a marked increase in device external quantum efficiency as measured in the forward direction, corresponding to the ratio of photons emitted to carriers injected. FIG. 7 shows the increase in efficiency with generation.

The device properties (maximum brightness and external quantum efficiency) are summarised in Table 1 for materials 0 and 3.

TABLE 1

Comparison of single layer efficiency and brightness data.

| Metal cathode | | 0 | | 3 | |
|---|---|---|---|---|---|
| Al | Efficiency (%) | 0.00025 | | 0.01 | |
|  | Brightness (Cd/m$^2$) | 1 | set A | 16 | set B |
| MgAl | Efficiency (%) | 0.02 | | 0.2 | |
|  | Brightness (Cd/m$^2$) | 24 | set B | 100 | set B |

Efficiencies are given in percent photons/electrons. With the given spectral distribution of emission of these materials, efficiencies may also be quoted in Cd/A with 1 Cd/A equivalent to an efficiency of 0.4%. It can be seen from Table 1 that not only the efficiency but also the maximum brightness depends on dendrimer generation. This is due to the large currents which are supported by the low generation materials due to extensive overlap of adjacent p orbitals and ease of current flow. However, large currents lead to ohmic heating of the material which in turn gives rise to degradation and limits the maximum achievable brightness. It is shown below that in the case of bilayer devices the improved transport properties of low generation materials can be put to use when a sufficiently high electron current is supported.

Control of Mobility—Mobility Measurements

In the following the direct control of mobility through dendrimer generation is demonstrated. The mobility is measured directly by the time of flight (TOF) technique in thin layers of the film (typically 200 nm) in conjunction with a rhodamine charge generation layer. Dendrimer films are spin-coated onto ITO substrates. Subsequently a 15 nm rhodamine film (R6G) is evaporated onto the dendrimer film, followed by patterned aluminium electrodes. Charges are generated within the rhodamine layer by a 550 nm 10 ns light pulse from an optical parametric oscillator pumped by a Q-switched Nd:YAG laser and swept across the dendrimer film by the application of a DC field. The transient current is measured using a digital oscilloscope and gives information about the carrier transit times as a function of applied field.

Figure 8:
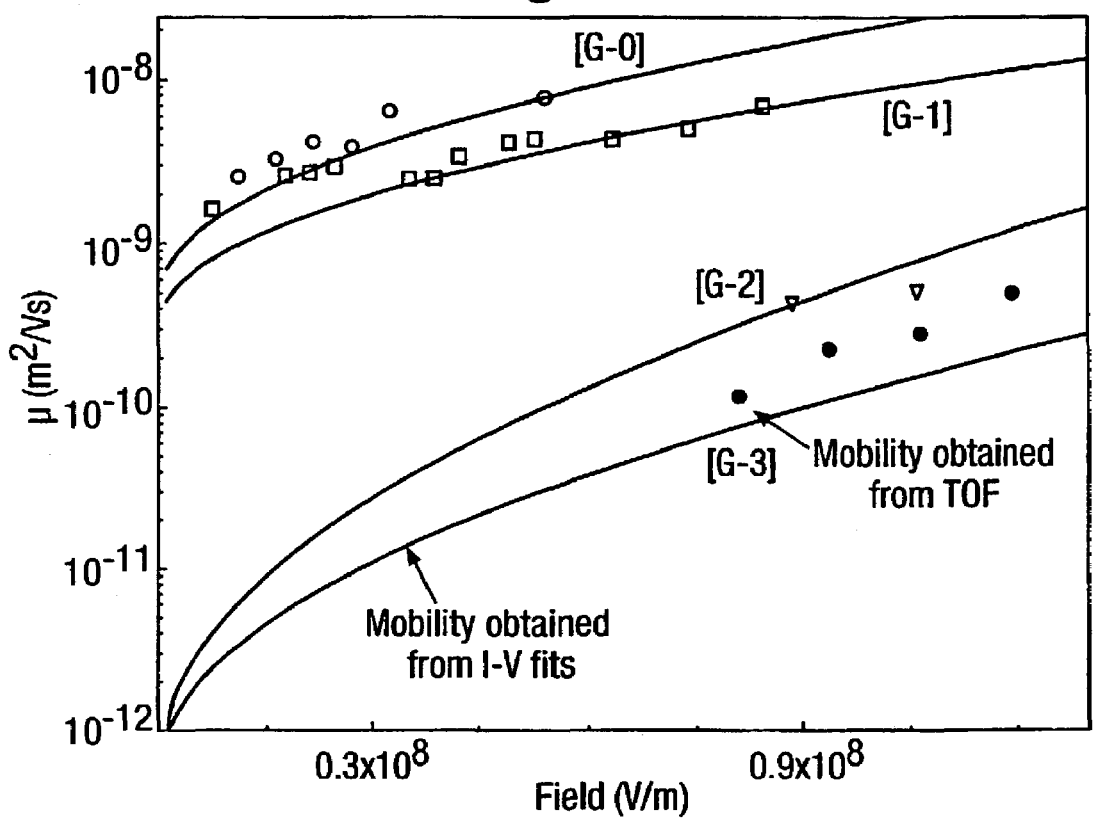
FIG. 8 shows mobility values obtained by current-field fits and the TOF method.

A further indirect way of estimating the mobility comes from the change of the current-field characteristics with generation. Current-field characteristics can be fitted using the barrier height to injection in a Schottky model and a field dependent mobility of the form $m_0 * \exp((E/E_0)^{0.5})$. Values obtained by this method agree quantitatively with mobility values obtained by the TOF method as shown in FIG. 8.

These measurements demonstrate that it is possible to tune majority carrier (hole) mobility by up to two orders of magnitude by changing the separation between adjacent chromophores through dendron branching. The dendrimer concept hence allows independent tuning of colour and transport, where the colour is governed by the chromophore photophysical properties and the transport is controlled by the spatial separation introduced by the dendrons. In the following section the benefits of controlling mobility are demonstrated in the context of bilayer LEDs, where, depending on the desired application, either high or low mobility materials may be required.

Bi-layer Devices (set B)

In the following the use of the family of dendrimers as hole transport layers in bilayer devices with vacuum deposited molecular materials is demonstrated. The device structure used was ITO/dendrimer/Alq3/metal. Devices were prepared as described above with vacuum deposited layers of the organic electron transporter (typically 50 nm, with dendrimer film thicknesses ~80 nm, spun at 1600 rpm). Patterned cathodes were evaporated either from aluminium or from a mixture of aluminium and magnesium. Device areas were 4 mm$^2$.

Figure 9:
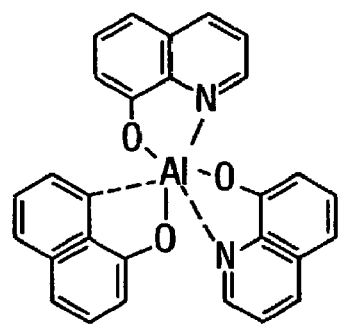
FIG. 9 shows the chemical structure of Alq3.

The chemical structure of Alq3 is shown in FIG. 9.

Devices with an Alq3 Layer

The dendrimer performed as a hole transporter in bilayers with Alq3. Emission was observed purely from the Alq layer. Table 2 summarises the results obtained for Alq3 bilayer devices.

TABLE 2

Comparison of dendrimer/Alq3 bilayer efficiency and brightness data.

| Metal cathode | | 0 | 3 |
|---|---|---|---|
| Al | Efficiency (%) | 0.1 | 0.3 |
|  | Brightness (Cd/m$^2$) | 600 | 150 |
| MgAl | Efficiency (%) | 0.1 | 0.2 |
|  | Brightness (Cd/m$^2$) | 2200 | 590 |

It can be seen that the efficiency is virtually independent of the metal electrode used. The lower mobility 3 gives a larger efficiency but limits the overall device current. The overall device current is also limited by the cathode, as the greatest brightness is achieved for the MgAl cathode with 0 as hole transporter. This brightness is comparable to values reported in hybrid systems with PVK (poly(vinyl carbazole)) as a hole transporting layer (Synthetic Metals 87, 175 (1997)).

Figure 10:
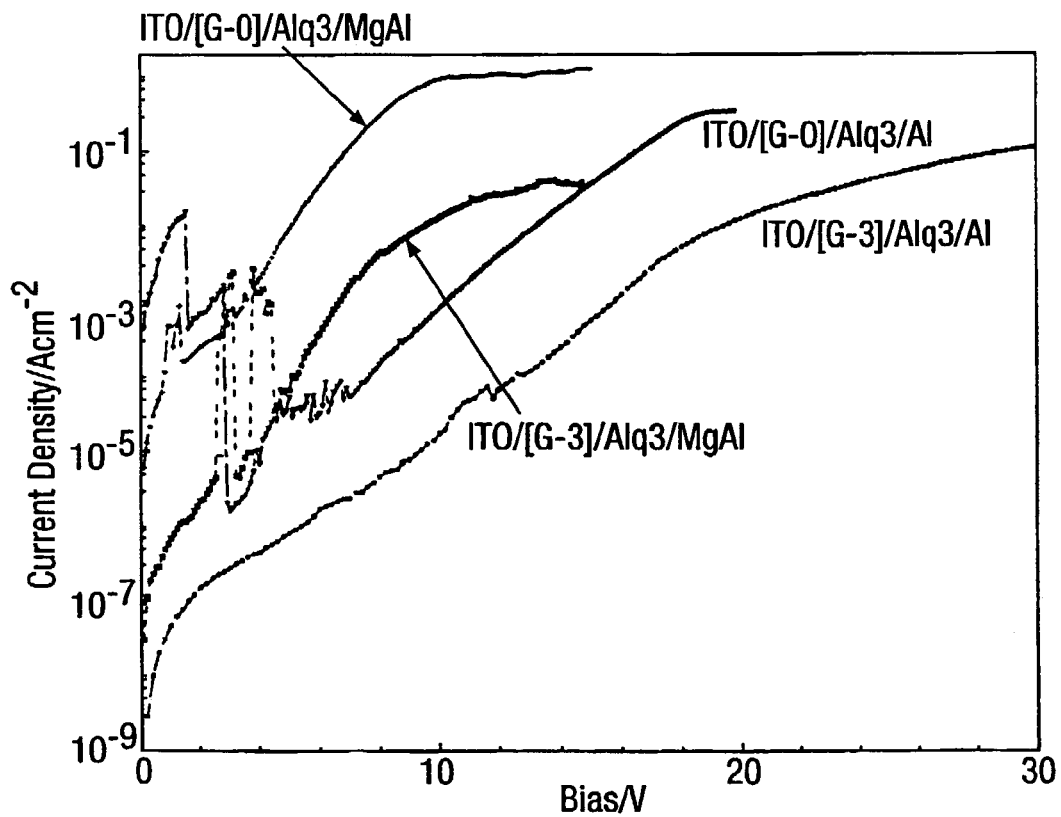
FIG. 10 shows the current-voltage characteristics for different device configurations.

FIG. 10 shows the current-voltage characteristics for different device configurations. It is seen that devices with 0 can support larger currents and also show lower operating biases, which is a direct result of the larger mobility of the dendrimer. A further reduction in operating bias is achieved through the change of electrode material.

Figure 11:
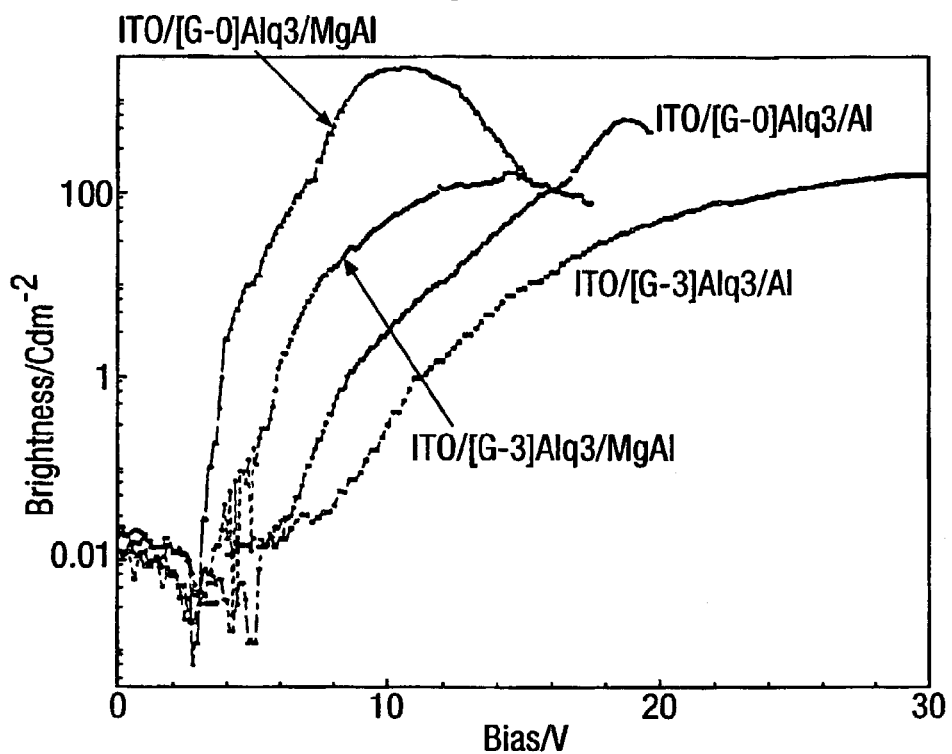
FIG. 11 shows the corresponding voltage-brightness characteristics.

The corresponding voltage-brightness characteristics are shown in FIG. 11, which follow a similar pattern. The trend to higher biases with higher dendrimer generation is also observed here. The barrier for electron injection from aluminium into Alq3 appears to be a current limiting factor at lower biases. At higher biases the hole current supported by the high generation dendrimer material is current and brightness limiting, as the maximum currents and brightnesses achieved for this case are independent of the electrode. It should be noted that the barrier to hole injection remains unchanged with generation, as electrochemical studies of the dendrimers revealed no change in oxidation potential with generation.

Figure 12:
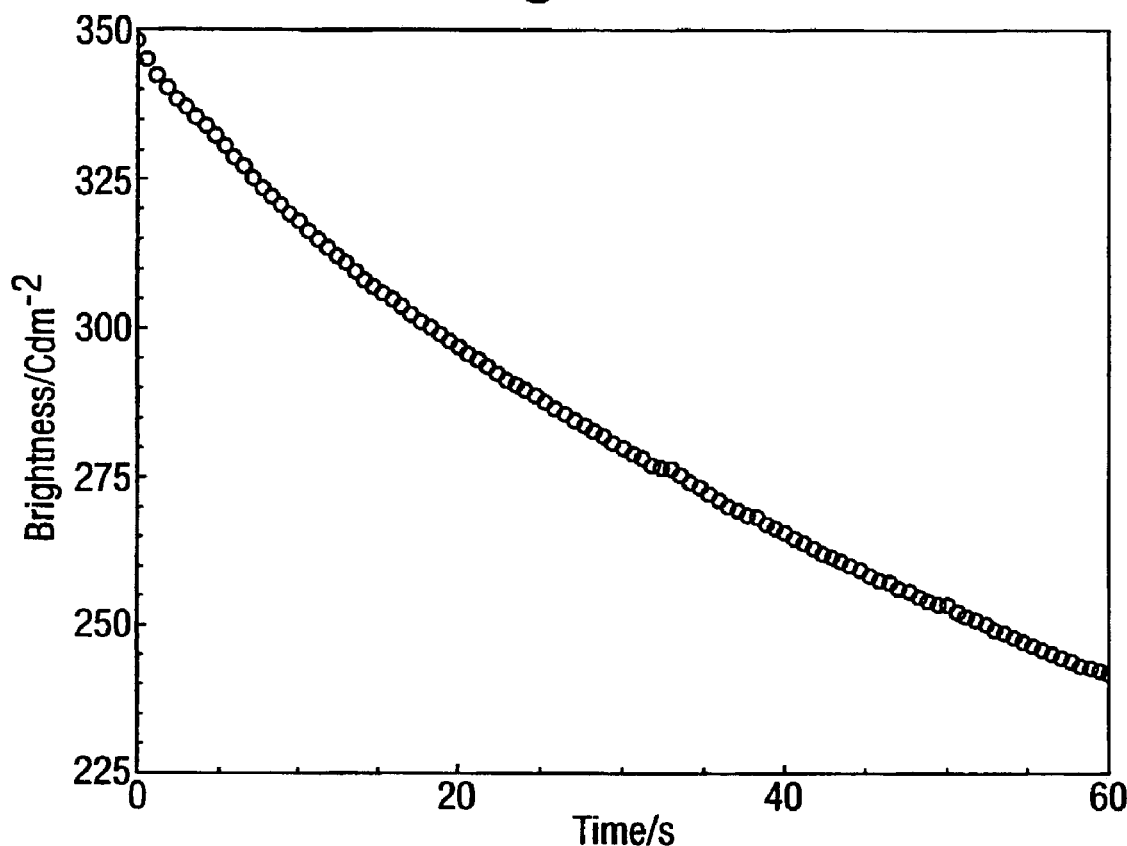
FIG. 12 shows the development of brightness over 60 seconds.

The devices are relatively stable in air, which is surprising considering the inherent instability to oxidation of many phenylene-vinylene compounds. The development of the brightness over 60 seconds is displayed in FIG. 12. Commercial use of this material would involve encapsulation to extend this lifetime greatly.

Bilayers with PBD as an Electron Transporter

Figure 13:
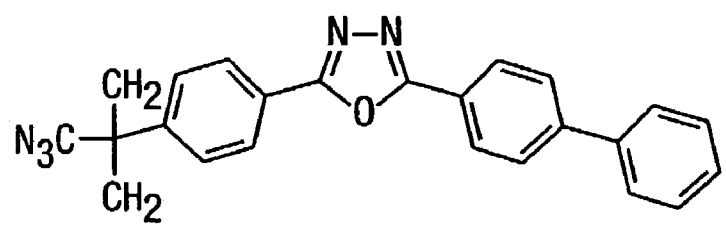
FIG. 13 shows the chemical structure of PBD.

Devices were fabricated in the configuration ITO/dendrimer/PBD/metal. The chemical structure of PBD is given in FIG. 13.

In the case of bilayers with wide gap PBD, emission was observed purely from the dendrimer. The results are summarised in Table 3.

TABLE 3

Comparison of dendrimer/Alq3 bilayer efficiency and brightness data.

| Metal cathode | | 0 | 3 |
|---|---|---|---|
| Al | Efficiency (%) | 0.07 | 0.4 |
|  | Brightness (Cd/m$^2$) | 60 | 65 |
| MgAl | Efficiency (%) | 0.2 | 0.4 |
|  | Brightness (Cd/m$^2$) | 93 | 65 |

In comparison to single layer dendrimer emitters, the efficiency increases by a factor of 300 for 0 and a factor of 40 for 3. The maximum brightness is increased dramatically for 0 and by at least a factor of 5 for 3. It is seen that the efficiency more than doubles as the mobility of the hole transporter is decreased, but remains virtually independent of the cathode material. Also, in contrast to the devices with Alq3, the maximum brightness and current do not show a strong dependence on either generation or on cathode material.

It is to be expected that the barrier for electron injection from PBD to the dendrimer is considerably larger than for Alq3, which may be a further reason for the relatively low currents and high operating fields in comparison to the Alq3 devices (see below).

Devices with an organolanthanide layer

Figure 14:
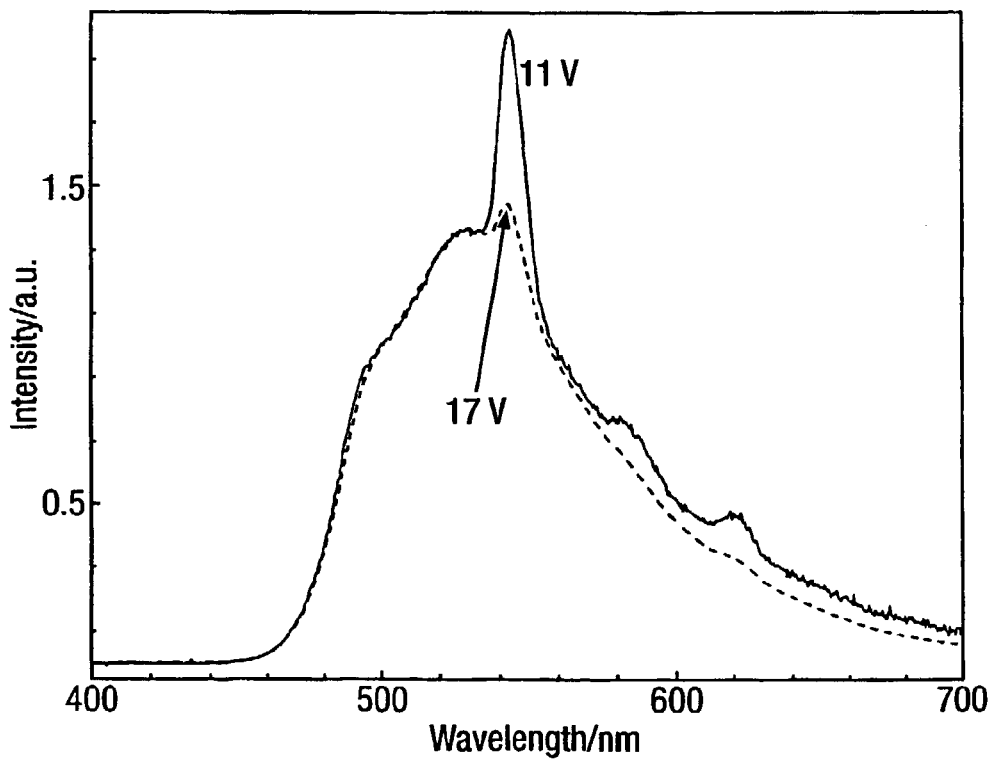
FIG. 14 shows the EL spectrum for a device according to the invention.

Bilayer devices were also prepared with an organolanthanide layer of MeTb13, which is a green phosphor, in the configuration ITO/dendrimer/MeTb13/MgAl. The emission was found to come from both the organolanthanide and the dendrimer, although at high currents the dendrimer emission dominated. The EL spectrum is given in FIG. 14 for a 3/MeTb13/MgAl device at 11 V and 17 V, corresponding to currents of 75 mA and 1.4 mA.

Figure 23:
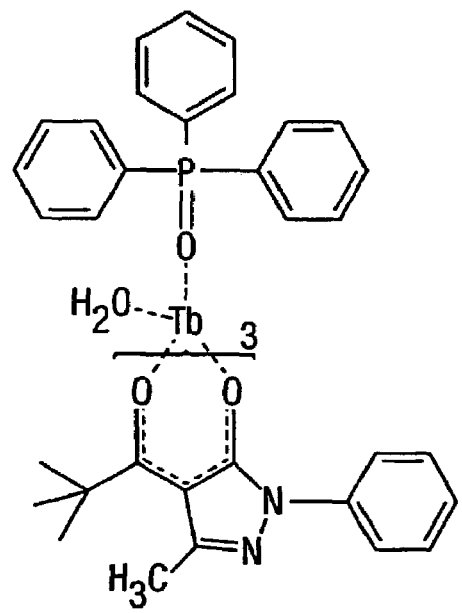
FIG. 23 shows the chemical structure of MeTb13.

The chemical structure of MeTb13 is shown in FIG. 23.

The brightnesses and efficiencies are summarised in Table 4

TABLE 4

Comparison of bilayer efficiency and brightness data.

| Metal cathode | | 0 | 3 |
|---|---|---|---|
| MgAl | Efficiency (%) | 0.008 | 0.2 |
|  | Brightness (Cd/m$^2$) | 50 | 128 |

It is seen that the efficiency increases significantly with generation, which suggests that limiting the hole current raises the efficiency and also leads to much improved carrier confinement at the interface.

Comparison of Device Characteristics

Figure 15:
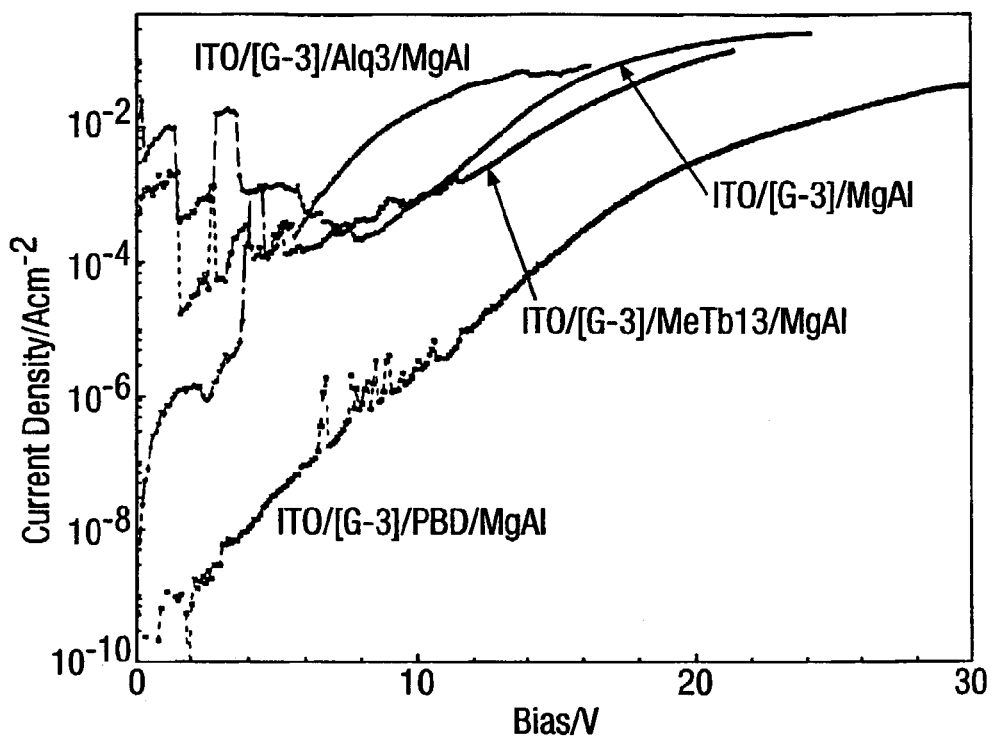
FIG. 15 shows a comparison of devices made with different electron transport layers.

A comparison of devices made with different electron transport layers with single layer devices as shown in FIG. 15 yields valuable information on the charge carrier blocking nature or current enhancing effect of the different layers. The largest current in 3 is supported by the single layer device, which exhibits characteristics similar to the device incorporating an organolanthanide layer. The electron current supported by Alq3 clearly increases the overall device current, which leads to a significant reduction in operating bias. In contrast, the larger band gap PBD shows much poorer electron transport properties than Alq, which gives rise to overall extremely low currents, particularly at biases below 10 V. Thus PBD acts as a very efficient hole blocker which helps to accumulate holes in the dendrimer at the dendrimer/PBD interface and likewise 3 efficiently blocks electrons.

Figure 16:
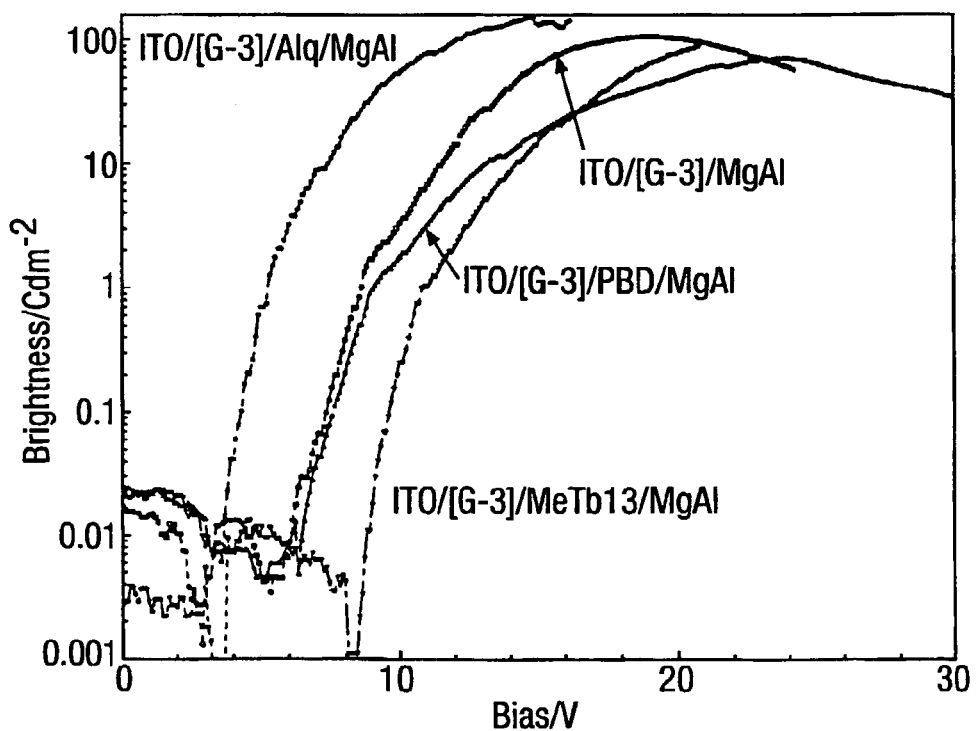
FIG. 16 shows the brightness-voltage characteristics for a number of devices.

The corresponding brightness-voltage characteristics are shown in FIG. 16. It is clear that the bilayer device using PBD is the most efficient configuration, certainly at low biases, as the light output closely follows the single layer emission, yet the current is much reduced. In the Alq3 device, the turn-on field for light emission is halved with respect to the single layer, whereas it is increased with the organolanthanide. The maximum brightnesses are all comparable, which suggests that this is a drawback of increasing efficiency through decreasing mobility. However, for many applications such as backlights, efficiency is more important than brightness, and brightnesses of 100 Cd/m$^2$ with good efficiencies are entirely acceptable.

Extreme Carrier Confinement

Figure 17:
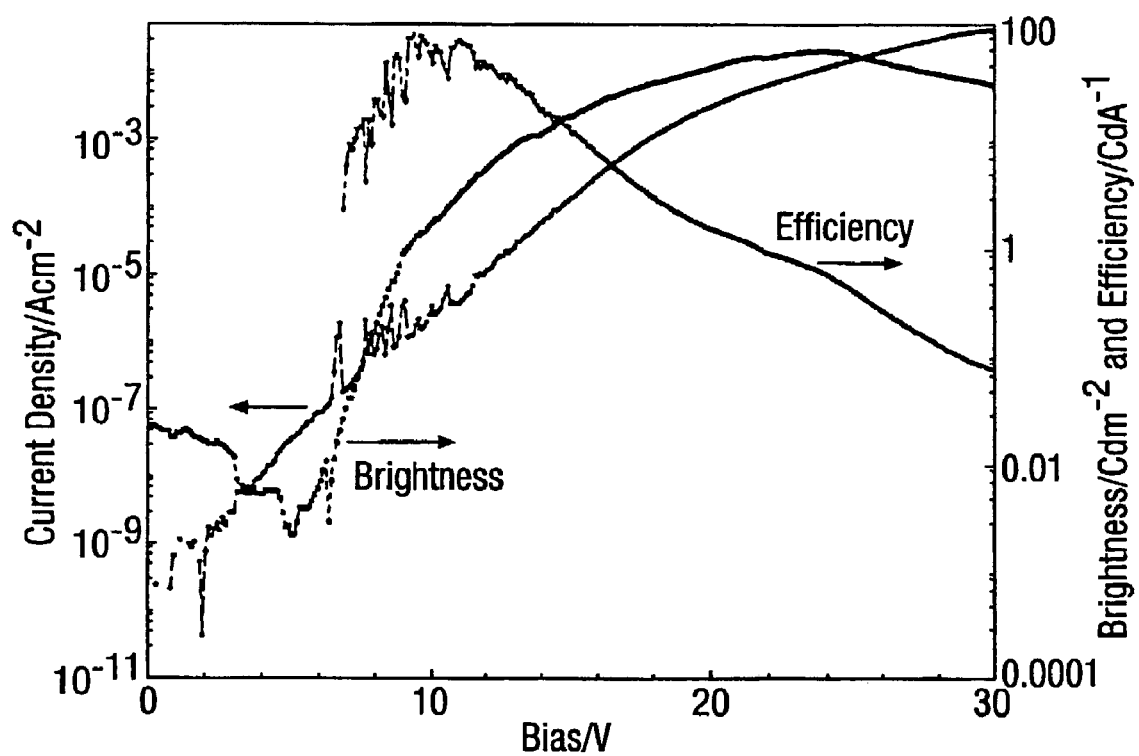
FIG. 17 shows the current-voltage characteristics of a bilayer device of the invention.

The low hole mobility of 3 and the even lower electron mobility allow for extreme carrier confinement at the interface to the larger bandgap PBD. This is demonstrated by the current-voltage characteristics of a ITO/3/PBD/MgAl bilayer device as seen in FIG. 17. Currents down to $10^{-11}$ A are measured at low biases and light emission is observed for currents between 10 nA and 100 nA. This gives rise to extremely large efficiencies, which are estimated to be up to 60 Cd/A, although this may be an overestimate due to a non-linearity of the detector at low intensities. At higher currents the device efficiency decreases steadily, but at a brightness of 55 Cd/m$^2$ an efficiency of 0.4% is measured.

EXAMPLE 6

1,3,5-Tris(4-bromophenyl)benzene

Silicon tetrachloride (9.7 ml, 85 mmol) was added dropwise over 15 min. to a mixture of the (partially dissolved) 4-bromophenylmethylketone (5.61 g, 28.2 mmol) in ethanol (22 ml) cooled in an ice bath. The temperature rose to 20° C. and the mixture darkened and thickened. The mixture was stirred at room temperature for 53 h (after 3 h dry THF (15 ml) was added). Water (50 ml) was then added carefully and dichloromethane (250 ml). The organic layer was separated, dried over sodium sulphate, filtered, and the solvent removed to leave a yellow solid. Recrystallisation from dichloromethane gave 1,3,5-tris(4-bromophenyl)benzene (2.85 g, 56%) as a white crystalline solid, mp 254–255° C.; $\delta_H$(200 MHz, CDCl3) 7.54 and 7.62 (12H, AA'BB', 2', 3', 5', 6'-H), 7.70 (3H, s, 2, 4, 6-H); m/z (CI) 541.9 (M+, 100%)—isotopic cluster of molecular ions.

Tris-aldehyde Benzene Core 1,3,5-Tris(4"-formylstilbene)benzene

A mixture of 4-vinylbenzaldehyde (1.95 g, 14.7 mmol), dimethylacetamide (40 ml), 1,3,5-tris(4'-bromophenyl)benzene (2.00 g, 3.68 mmol), trans-di((-aceto)-bis[o-(di-o-tolylphosphino)benzyl] dipalladium (II) (10 mg, 11 m (mol), 2,6-di-tert-butyl-p-cresol (646 mg, 29.3 mmol), and sodium carbonate (1.56 g, 14.7 mmol) was degassed by sequential evacuation and purging with argon over 35 min. The mixture was then stirred at 130° C. for 50.5 h. Water (100 ml) and dichloromethane (100 ml) were added. The aqueous layer was separated and extracted with dichloromethane (3×100 ml, 2×50 ml, 2×100 ml). The combined organic layers were washed with water (3×500 ml) and brine (250 ml), dried over sodium sulphate, filtered and the solvent completely removed to leave a yellow/brown solid. Trituration from dichloromethane followed by recrystallisation from dichloromethane gave 1,3,5-tris(4"-formylstilbene)benzene (1.24 g, 48%) as a yellow powder, mp 163° C. (Found: C, 87.43; H, 5.36. $C_{51}H_{36}O$ requires C, 87.91; H, 5.21%); $v^{max}$(KBr)/cm$^{-1}$ 1690 (C=O); $\lambda_{max}$(CH2Cl2)/nm (log $\epsilon$ 237 (4.46), 358 (5.10); $\delta$H(500 MHz, CDCl3) 7.24 and 7.35 (6H, ABq, JAB=16.5 Hz, vinylic H), 7.69 and 7.77 (12H, AA'BB', 2', 3', 5', 6'-H), 7.71 and 7.91 (12H, AA'BB', 2", 3", 5", 6"-H), 7.86 (3H, s 2, 4, 6-H), 10.07 (3H, s, CHO); m/z (CI) 697.0 (MH+, 100%).

G0 Benzene-centred Dendrimer.

A solution of 1,3,5-tris(4"-formylstilbene)benzene (350 mg, 0.50 mmol), 1-(methylenedimethylphosphonate)-3,5-di-tert-butylbenzene (628 mg, 2.01 mmol), and potassium-tert-butoxide (225 mg, 2.01 mmol) in dry tetrahydrofuran (80 ml) was stirred in the dark under argon at room temperature for 17 h. A blue fluorescent tinge appeared in the solution. The solvent was removed and dichloromethane (150 ml) and water (100 ml) were added. The organic layer was separated and washed with brine (100 ml), dried over sodium sulphate, filtered, and the solvent removed. The residue was purified by column chromatography over silica using dichloromethane/light petroleum (1.5:3.5) as eluent to give the G0 dendrimer (520 mg, 82%) as a pale yellow powder. A sample for analysis was recrystallised from dichloromethane/methanol, mp 209–211° C. (Found C, 91.57; H, 8.41%. $C_{96}H_{102}$ requires C, 91.81; H, 8.19%); $\lambda_{max}$(CH2Cl2)/nm (log $\epsilon$ 246 (4.81), 375 (5.39), 390sh (5.29); $\delta$H(400 MHz, CDCl3) 1.39 (54H, s, t-butyl H), 7.12 and 7.21 (6H, ABq, 7'' and 8'' H), 7.22 (6H, s, 7' and 8' H), 7.38 (3H, m, 4''H), 7.40 (6H, d, J=1.5 Hz, 2''' and 6'''H), 7.57 (12H, s, 2'', 3'', 5'', 6''H), 7.67 and 7.75 (12H, AA'BB', 2', 3', 5'6'H) and 7.86 (3H, s, 2, 4, 6H); m/z (MALDI) 1255.9 (MH+, 100%).

EXAMPLE 7

Figure 24:
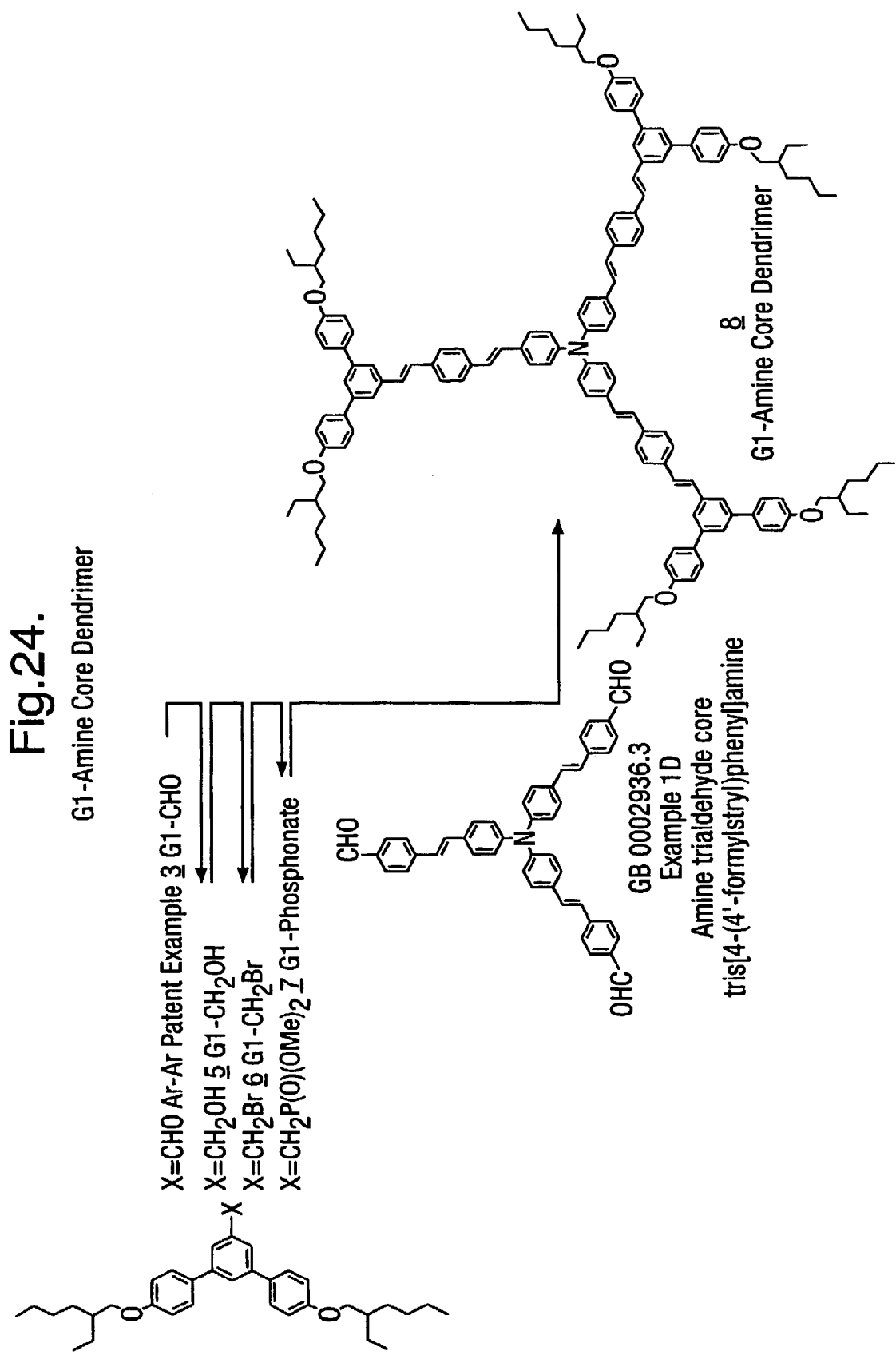
FIG. 24 shows a preferred dendrimer used in the invention and its syntheses.

The novel dendrimer 8 and reaction scheme are shown in FIG. 24.

Compound 5

G1-CH$_2$OH 3,5-Di[4'-2"-ethylhexyloxy)phenyl]benzyl alcohol

A mixture of the aryl benzaldehyde (Ar-Ar Patent: Example 3: G1-CHO: 3.5-di[4'(2"-ethylhexyloxy)phenyl] benzaldehyde (610 mg, 1.19 mmol), NaBH$_4$ (90 mg, 2.37 mmol), and 12.5 cm$^3$ of anhydrous THF was heated at reflux under argon for 5.3 h before being cooled and quenched with 5 cm$^3$ of H$_2$O. The two layers were separated. The aqueous layer was extracted with DCM (2×4 cm$^3$). The combined DCM extracts and the organic portion were dried (MgSO$_4$). The solvents were completely removed to leave a colourless oil. The oil was purified by column chromatography using silica gel with DCM-light petroleum (1:3 to 1:2) as eluent to give 501 mg (82%) of colourless oil of the desired alcohol (5); (Found: C, 81.4; H, 9.4 $C_{35}H_{48}O_3$ requires C, 81.4; H, 9.4%); $v_{max}$/cm$^{-1}$ (neat) 3325 (OH); $\lambda_{max}$(CH$_2$Cl$_2$)/nm 269 ($\epsilon$/dm$^3$mol$^{-1}$ cm$^{-1}$ 65455); $\delta_H$(400 MHz; CDCl$_3$) 0.88–1.00 (12H, m, Me), 1.29–1.62 (16H, m, CH$_2$), 1.68–1.84 (2H, m, 2×CH), 3.90 (4H, m, ArOCH$_2$), 4.82 (2H, s, ArCH$_2$), 7.00 (4H, m, ArH), 7.50 (2H, s, ArH), 7.58 (4H m, ArH), and 7.66 (1H s, ArH), NB: the OH is not easily observed; $\delta_c$(100 MHz; CDCl$_3$) 11.1, 14.1, 23.1, 23.9, 29.1, 30.5, 39.4, 65.5, 70.6, 114.8, 123.6, 124.6, 128.2, 133.2, 141.7, 141.8, and 159.1; m/z[MALDI] 516 (M$^+$).

Compound 6

G1-CH$_2$Br 3,5-Di[4'-(2"-ethylhexyloxy)phenyl]benzyl bromide

Phosphorus tribromide (0.7 cm$^3$, 7.37 mmol) was added slowly to a solution of the benzyl alcohol 5 (890 mg, 1.72 mmol) in dry DCM (37 cm$^3$) at room temperature under argon for 18 h. The mixture was diluted with water (10 cm$^3$). The organic layer was separated, washed with water (2×20 cm$^3$), brine (1×20 cm), dried over anhydrous magnesium sulfate, and the solvent completely removed to give yellowish oil. The residue was purified by column chromatography over silica with ethyl acetate-light petroleum (1:0 to 1:10) as eluent to give a white solid of 6 (805 mg, 81%); mp 79–79.5° C.; (Found: C, 72.6; H, 8.2 $C_{35}H_{47}BrO_2$ requires C, 72.5; H, 8.2%); $\lambda_{max}$(CH$_2$Cl$_2$)/nm 272 ($\epsilon$/dm$^3$mol$^{-1}$ cm$^{-1}$ 41332); $\delta_H$(400 MHz; CDCl$_3$) 0.91–1.02 (12H, m, Me), 1.31–1.68 (16H, m, CH$_2$), 1.74–1.87 (2H, m, CH), 3.93 (4H, m, ArOCH$_2$), 4.62 (2H, s, ArCH$_2$), 7.03 (4H, m, ArH), 7.53 (2H, m, ArH), 7.59 (4H, m, ArH), and 7.68 (1H, m, ArH); $\delta_c$(100 MHz; CDCl$_3$) 11.1, 14.1, 23.1, 23.9, 29.1, 30.5, 33.7, 39.4, 70.6, 114.8, 125.4, 125.7, 128.2, 132.8, 138.6, 142.0 and 159.3; m/z [MALDI] 500 (M$^+$-Br).

Compound 7

G1-Phosphonate 1-(Methylenedimethylphosphonate)-3,5-di[4'(2"-ethylhexyloxy)phenyl]benzene A mixture of the benzyl bromide 6 (800 mg, 1.38 mmol), and trimethyl phosphite (3.6 cm$^3$, 30.5 mmol) was heated at 110° C. under argon for 14 h. The mixture was allowed to cool and the excess of trimethyl phosphite was removed under vacuum. The light yellow residue was purified by column chromatography over silica gel with ethyl acetate-light petroleum (1:10) and then MeOH-DCM (0:1 to 1:10)

as eluent to give 840 mg (100%) of the G1-Phosphonate 7 as a colourless oil; (Found: C, 72.8; H, 8.7. $C_{37}H_{53}O_5P$ requires C, 73.0; H, 8.8%); $\lambda_{max}(CH_2Cl_2)$/nm 271 ($\epsilon$/dm$^3$ mol$^{-1}$ cm$^{-1}$ 16234); $\delta_H$(200 MHz; CDCl$_3$) 0.84–1.02 (12H, m, Me), 1.26–1.60 (16H, m, CH$_2$), 1.68–1.85 (2H, m, CH), 3.28 (2H, d, J 21.8 Hz, ArCH$_2$P), 3.72 (6H, d, J 10.8 Hz, OMe), 3.90 (4H, m, ArOCH$_2$), 6.99 (4H, m, ArH), 7.42 (2H, m, ArH), and 7.51–7.68 (5H, m, ArH); m/z [MALDI] 609 (MH$^+$).

Compound 8

G1 Amine 3 Core Dendrimer

A solution of G1-phosphonate (7) (500 mg, 0.821 mmol), tris[4-(4'formyl)styrylphenyl]amine (Example 1D) (131 mg, 0.205 mmol), potassium tert-butoxide (92 mg, 0.821 mmol) and anhydrous THF (22 cm$^3$) was stirred at room temperature for 14 h before being quenched with 3 cm$^3$ of water. The aqueous portion was separated and the organic layer was washed with brine (1×10 cm$^3$), dried (MgSO$_4$) and the solvent was completely removed to leave a yellow oil. The oil was purified over silica gel using ethyl acetate-light petroleum (1:10) as eluent to give 8 (406 mg, 95%) as a bright yellow solid; (Found: C, 86.3; H, 8.3; N, 0.8. $C_{150}H_{171}NO_6$ requires C, 86.5; H, 8.3; N, 0.7%); $\lambda_{max}$ (CH$_2$Cl$_2$)/nm 264 ($\epsilon$/dm$^3$ mol$^{-1}$ cm$^{-1}$150046), 287sh (133375), 345 (120870) and 424 (183389); $\delta_H$(400 MHz; CD$_2$Cl$_2$), 0.91–1.07 (36H, m, 12×Me), 1.34–1.67 (48H, m, 24×CH$_2$), 1.74–1.87 (6H, m, 6CH), 3.96 (12H, m, 6xArOCH$_2$), 7.04–7.70 (69H, ArH & vinyl H); m/z [MALDI] 2083 (M$^+$).

Device Preparation & Results

Figure 25:
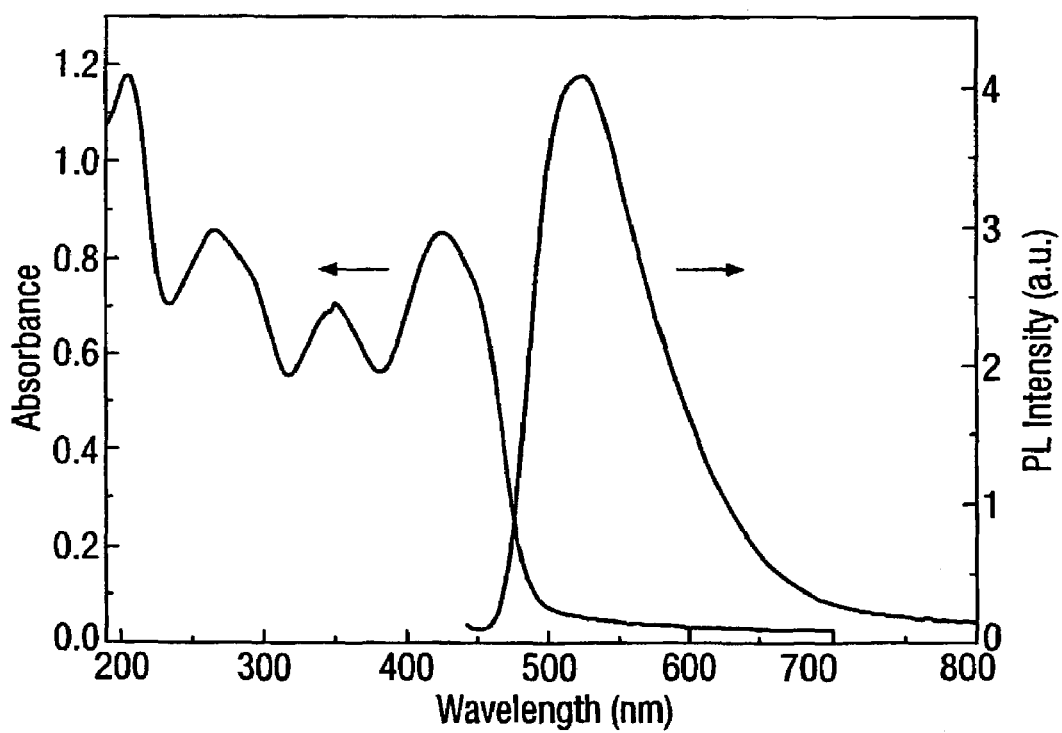
FIG. 25 shows the absorption and PL emission spectra of the dendrimer in FIG. 24.

Device fabrication & measurement was carried out as for the preceding set A devices. However, in addition to single layer devices several heterolayer devices were prepared. The heterolayer devices were prepared by sequentially depositing a PEDOT/PSS film, a layer of dendrimer, a layer of dendrimer blended with PBD and then an Al cathode onto the cleaned ITO substrate. The neat dendrimer layer was spin-coated at a spin speed of 1000 rpm and then the blended dendrimer:PBD layer was spin-coated onto the neat dendrimer layer at a spin speed of 2000 rpm. The dendrimer and dendrimer:PBD mixture were both dissolved in THF at a dendrimer concentration of 10 mg/ml. The absorption spectrum and PL emission spectrum of 8 are shown in FIG. 25. The performance of several devices containing 8 are summarised in the table below:

| Device structure | EL efficiency (%) | Brightness (cd/m$^2$) | Power efficiency (lm/W) |
|---|---|---|---|
| ITO/PEDOT/8/Al | 0.0005 | 4.5 | 0.000024 |
| ITO/PEDOT/8: PBD (1:0.8)/Al | 0.045 | 470 | 0.02 |
| ITO/PEDOT/8: PBD (1:0.8)/Al | 0.10 | 4700 | 0.08 |
| ITO/PEDOT/8: PBD (1:1)/Al | 0.17 | 2400 | 0.09 |

Spectra for the heterolayer device ITO/PEDOT/8/8: PBD (1:0.8)/Al are shown in FIGS. 26–28.

Figure 26:
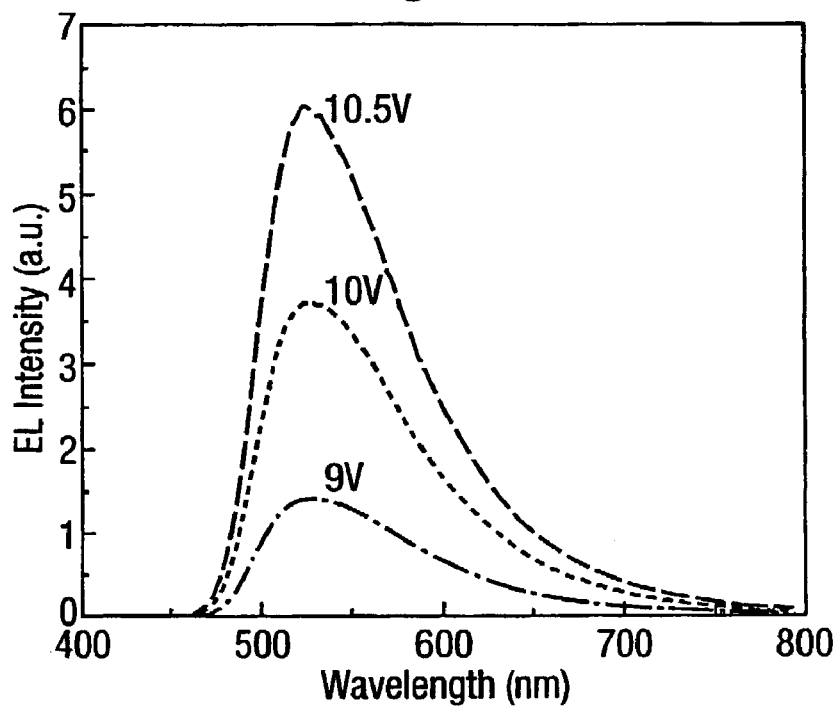
FIG. 26 shows the electroluminescence spectrum for a heterolayer device containing the dendrimer of FIG. 24 in a 1:0.8 ratio with PBD.

FIG. 26, shows the electroluminescent emission spectrum at different voltages of the device ITO/PEDOT/8/8: PBD (1:0.8)/Al.

Figure 27:
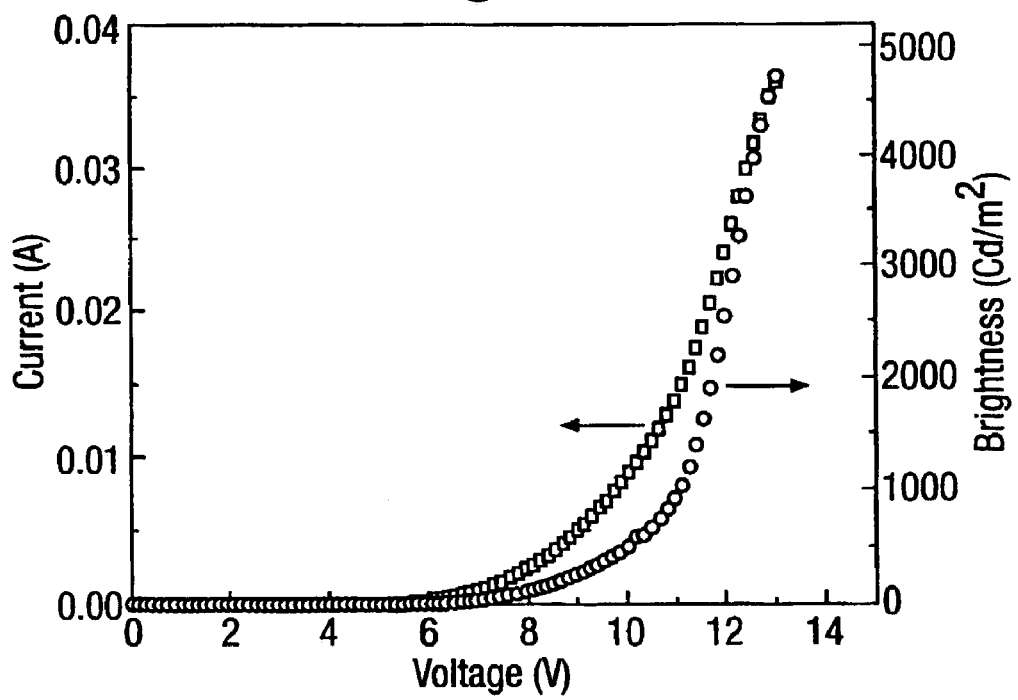
FIG. 27 shows the current-voltage luminescent characteristics for this device.

FIG. 27 shows the current-voltage-luminescent characteristics.

Figure 28:
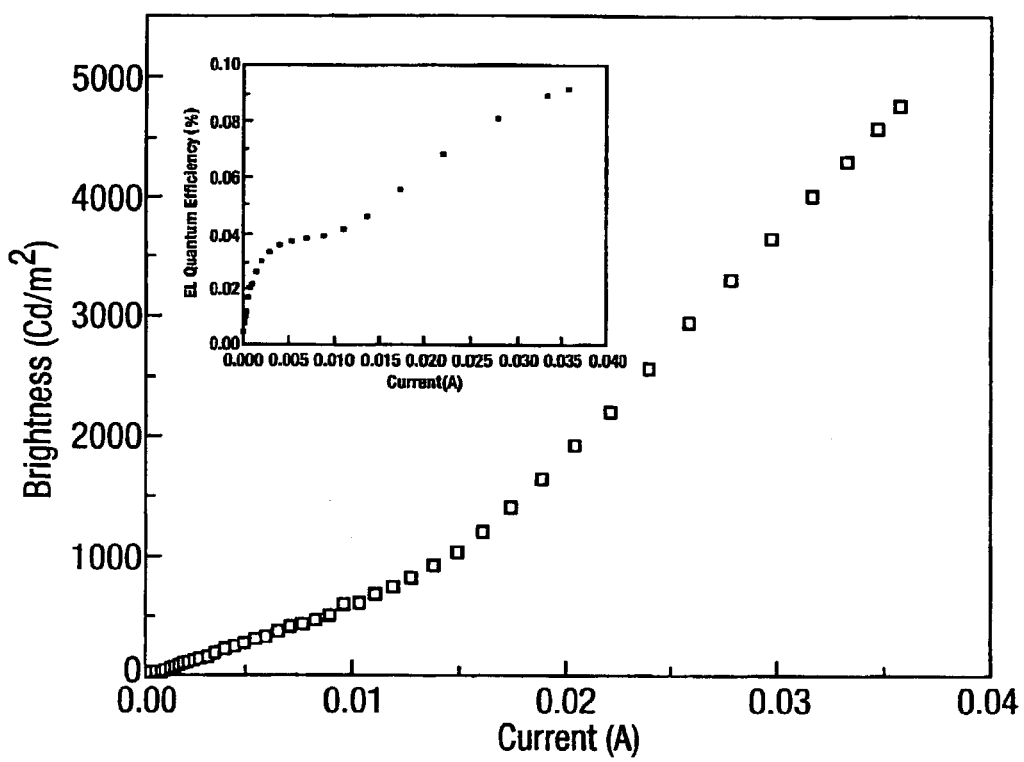
FIG. 28 shows the current luminance efficiency characteristics for this device.

FIG. 28 shows the current-luminance-efficiency characteristics.

Figure 29:
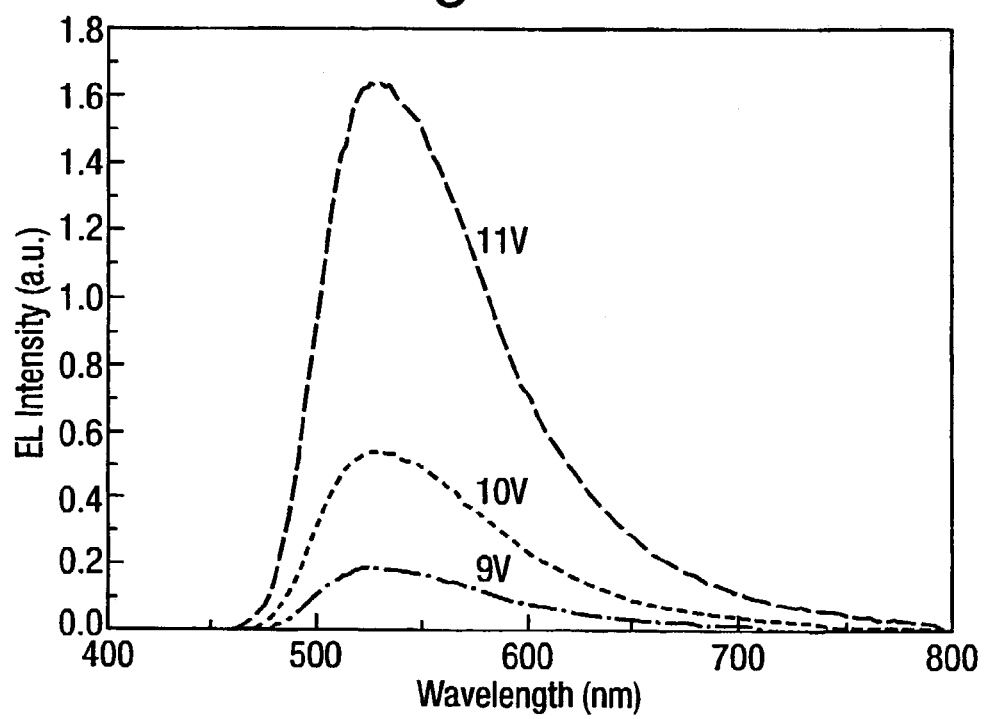
FIG. 29 shows the electroluminescence spectrum for a heterolayer device containing the dendrimer of FIG. 24 in a 1:1 ratio with PBD.
Figure 30:
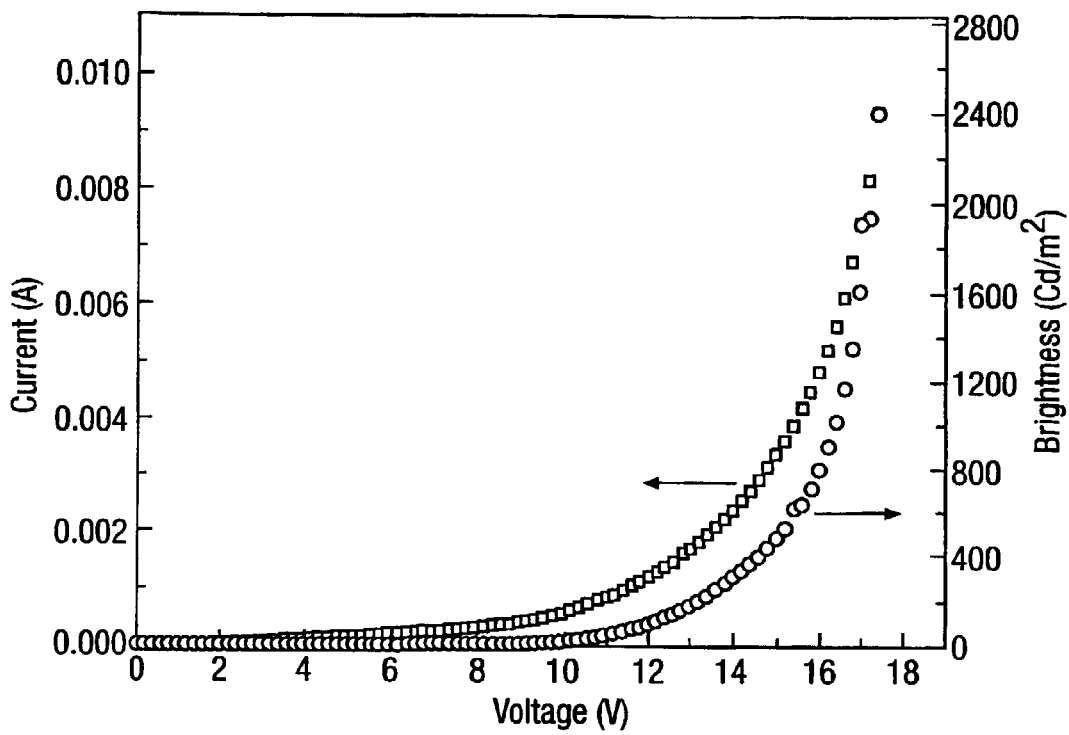
FIG. 30 shows the current-voltage luminescent characteristics for this device.
Figure 31:
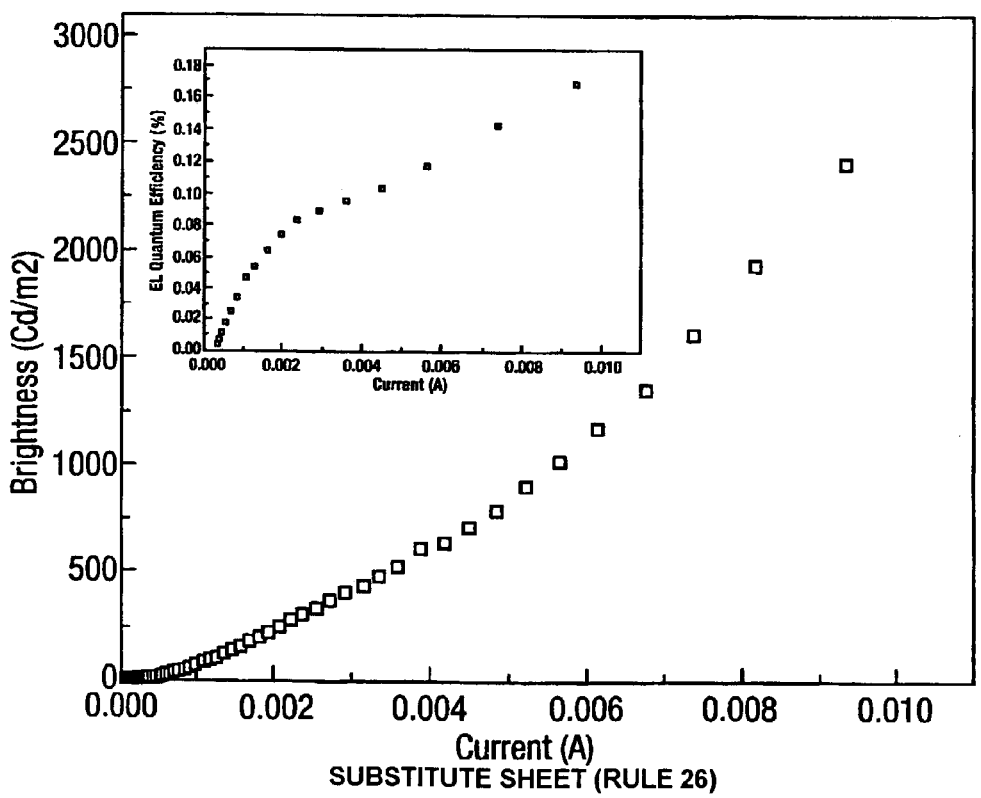
FIG. 31 shows the current luminance efficiency characteristics for this device.

Spectra for the heterolayer device ITO/PEDOT/8/8: PBD (1:1)/Al are shown in FIGS. 29–31. Changing the concentration of PBD in the blend has increased the maximum efficiency, although decreased the maximum brightness.

FIG. 29 shows the electroluminescent emission spectrum at different voltages.

FIG. 30 shows the current-voltage-luminescent characteristics.

FIG. 31 shows the current-luminance-efficiency characteristics.

The invention claimed is:

1. A light emitting device comprising at least one compound of the formula:

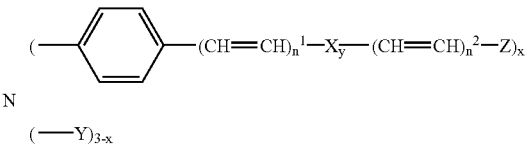

where x is 3, 2 or 1, y is 0 or 1, $n^1$ and $n^2$, which may be the same or different, are 0 or 1 to 3, X represents a divalent mono- or poly-aromatic moiety or a divalent mono- or poly-heteroaromatic moiety or combinations thereof, the or each Y, which may be the same or different if x is 1, represents hydrogen or an optionally substituted hydrocarbon group, Z represents an at least partly conjugated dendritic molecular structure comprising aromatic or heteroaromatic groups or combinations thereof and, optionally, additionally comprising alkenylene groups, the aromatic or heteroaromatic groups or combinations thereof being connected to each other either via a ring carbon atom of an aromatic or heteroaromatic group to a ring carbon atom of another aromatic or heteroaromatic group or, if an alkenylene group is present via, a ring carbon atom of an aromatic or heteroaromatic group to a carbon atom of an alkylene group, said dendritic molecular structure being connected to the remainder of the molecule via a ring carbon atom of an aromatic or heteroaromatic group to which more than one at least partly conjugated dendritic chain is attached, one or more of the aromatic or heteroaromatic rings of the dendrimers optionally being substituted, and where Z or the remainder of the molecule or both, excluding any groups Y, is luminescent, and with the proviso that when $n^2$ is 0, x must be 3.

2. A device according to claim 1 wherein the compound is luminescent in the solid state.

3. A device according to claim 2 wherein the compound emits light in the visible region under electrical or optical excitation.

4. A device according to claim 1 wherein the compound has more than one luminescent moiety and the energy resulting from electrical or optical excitation is transferred to one of them for light emission.

5. A device according to claim 1 wherein the compound has at least two at-least-partly-conjugated luminescent moieties, the luminescent moiety or moieties further from the core being of larger HOMO-LUMO energy gap than the luminescent moiety or moieties closer to the core.

6. A device according to claim 5, wherein the or each Z contains more than one luminescent moiety.

7. A device according to claim 5 wherein the compound has a luminescent moiety which is not part of Z and has a smaller inherent HOMO-LUMO energy gap than the other luminescent moiety or moieties.

8. A device according to claim 1 wherein a luminescent moiety is part of Z.

9. A device according to claim 8 wherein the luminescent moiety or moieties further from the core have larger HOMO-LUMO energy gaps than those closer to the core.

10. A device according to claim 1 wherein at least one surface group is attached to a distal aryl ring carbon atom of Z, said group being a further-reactable alkene, (meth)acrylate, sulphur-containing, or silicon-containing group; sulphonyl group; polyether group; $C_1$-to-$C_{15}$ alkyl group; —$NH_2$ group; mono-, di- or tri-$C_1$-to-$C_{15}$ alkyl amine group; —COOR group wherein R is hydrogen or $C_1$-to-$C_{15}$ alkyl; —OR group wherein R is hydrogen, aryl, or $C_1$-to-$C_{15}$ alkyl or alkenyl; $O_2SR$ group wherein R is $C_1$-to-$C_{15}$ alkyl or alkenyl; —SR group wherein R is aryl, or $C_1$-to-$C_{15}$ alkyl or alkenyl; —$SiR_3$ groups wherein the R groups are the same or different and are hydrogen, $C_1$-to-$C_{15}$ alkyl or alkenyl; aryl group or heteroaryl group.

11. A device according to claim 10 wherein the surface group or groups is/are t-butyl groups.

12. A device according to claim 1 wherein the first aryl moiety of Z is a 1, 3, 5-bonded benzene ring.

13. A device according to claim 12 wherein Z is 3,5-bis(3',5'-di-t-butylstyryl)phenyl, 3,5-bis[3",''-di-t-butylstyryl)styryl]phenyl or 3,5-bis{3',5'-bis[3",5"-bis(3''',5'''-dibutylstyryl)styryl]styryl}phenyl.

14. A device according to claim 1 wherein x is 3.

15. A device according to claim 1 wherein $n^1$ and $n^2$ are 1.

16. A device according to claim 1 wherein X comprises a moiety of benzene, anthracene, pyridine, pyrimidine, triazine, thiophene, oxadiazole or coronene.

17. A device according to claim 1 wherein X is connected to the adjacent atoms in the para position.

18. A device according to claim 1 wherein the compound incorporates one or more electron-withdrawing groups which increase its electron-transporting properties.

19. A device according to claim 1 wherein the compound forms a light-emitting layer.

20. A device according to claim 1 wherein the compound forms a hole-transporting layer.

* * * * *